US010793570B2

(12) United States Patent
Ochiana et al.

(10) Patent No.: US 10,793,570 B2
(45) Date of Patent: Oct. 6, 2020

(54) METHODS AND REAGENTS FOR RADIOLABELING

(71) Applicant: Memorial Sloan-Kettering Cancer Center, New York, NY (US)

(72) Inventors: Stefan O. Ochiana, Chevy Chase, MD (US); NagaVaraKishore Pillarsetty, Jackson Heights, NY (US); Tony Taldone, Forest Hills, NY (US); Gabriela Chiosis, New York, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 0 days.

(21) Appl. No.: 16/396,496

(22) Filed: Apr. 26, 2019

(65) Prior Publication Data
US 2020/0017502 A1 Jan. 16, 2020

Related U.S. Application Data

(62) Division of application No. 15/971,908, filed on May 4, 2018, now Pat. No. 10,329,293, which is a division of application No. 15/107,229, filed as application No. PCT/US2014/072090 on Dec. 23, 2014, now Pat. No. 9,994,573.

(60) Provisional application No. 61/919,901, filed on Dec. 23, 2013.

(51) Int. Cl.
C07D 473/34 (2006.01)
C07F 7/22 (2006.01)
C07B 59/00 (2006.01)

(52) U.S. Cl.
CPC .......... C07D 473/34 (2013.01); C07B 59/002 (2013.01); C07F 7/2208 (2013.01); C07B 2200/05 (2013.01)

(58) Field of Classification Search
CPC .................................................. C07D 473/34
See application file for complete search history.

(56) References Cited

U.S. PATENT DOCUMENTS

| | | | |
|---|---|---|---|
| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |
| 7,834,181 B2 | 11/2010 | Chiosis et al. |
| 8,586,605 B2 | 11/2013 | Cai et al. |
| 8,703,942 B2 | 4/2014 | Chiosis et al. |
| 9,328,114 B2 | 5/2016 | Chiosis et al. |
| 9,346,808 B2 | 5/2016 | Sun et al. |
| 9,403,828 B2 | 8/2016 | Chiosis |
| 9,546,170 B2 | 1/2017 | Taldone et al. |
| 9,555,137 B2 | 1/2017 | Chiosis et al. |
| 9,701,678 B2 | 7/2017 | Chiosis et al. |
| 9,926,321 B2 | 3/2018 | Sun et al. |
| 9,994,573 B2 | 6/2018 | Ochiana et al. |
| 10,000,494 B2 | 6/2018 | Chiosis |
| 10,064,867 B2 | 9/2018 | Taldone et al. |
| 10,167,285 B2 | 1/2019 | Chiosis et al. |
| 10,172,863 B2 | 1/2019 | Chiosis et al. |
| 10,329,293 B2 | 6/2019 | Ochiana et al. |
| 10,336,757 B2 | 7/2019 | Chiosis et al. |
| 10,421,758 B2 | 9/2019 | Chiosis et al. |
| 2007/0178537 A1 | 8/2007 | Chiosis et al. |
| 2008/0253965 A1 | 10/2008 | Chiosis et al. |
| 2009/0298857 A1 | 12/2009 | Chiosis et al. |
| 2010/0016586 A1 | 1/2010 | Bajji et al. |
| 2010/0292255 A1 | 11/2010 | Bajji et al. |
| 2011/0104054 A1 | 5/2011 | Chiosis et al. |
| 2011/0312980 A1 | 12/2011 | Chiosis |
| 2012/0208806 A1 | 8/2012 | Chiosis et al. |
| 2014/0045867 A1 | 2/2014 | Taldone et al. |
| 2014/0088121 A1 | 3/2014 | Sun et al. |
| 2014/0227183 A1 | 8/2014 | Chiosis et al. |
| 2014/0242602 A1 | 8/2014 | Chiosis et al. |
| 2014/0294725 A1 | 10/2014 | Chiosis et al. |
| 2014/0315929 A1 | 10/2014 | Chiosis |
| 2014/0378452 A1 | 12/2014 | Chiosis |
| 2016/0194328 A1 | 7/2016 | Chiosis et al. |
| 2016/0264577 A1 | 9/2016 | Sun et al. |
| 2016/0310497 A1 | 10/2016 | Chiosis et al. |
| 2016/0333014 A1 | 11/2016 | Chiosis |
| 2017/0029426 A1 | 2/2017 | Ochiana et al. |
| 2017/0151247 A1 | 6/2017 | Taldone et al. |
| 2017/0342073 A1 | 11/2017 | Chiosis et al. |
| 2018/0251461 A1 | 9/2018 | Ochiana et al. |

(Continued)

FOREIGN PATENT DOCUMENTS

| | | |
|---|---|---|
| WO | WO-96/05309 A2 | 2/1996 |
| WO | WO-2006/084030 A2 | 8/2006 |
| WO | WO-2007/134298 A2 | 11/2007 |

(Continued)

OTHER PUBLICATIONS

U.S. Appl. No. 15/377,663.
U.S. Appl. No. 15/620,865, Chiosis et al.
Chiosis, G. et al, STN International, HCAPLUS database (Columbus, OH), Accession No. 2006: 791015 (2006).
Chiosis, G. et al, STN International, HCAPLUS database (Columbus, OH), Accession No. 2013: 83108 (2013).
Farina, V. et al, The Stille reaction: Chapter 1, Organic Reactions, 50, 384 pages (1997).

(Continued)

*Primary Examiner* — Golam M Shameem
(74) *Attorney, Agent, or Firm* — Choate, Hall & Stewart LLP; Brenda Herschbach Jarrell; John P. Rearick

(57) ABSTRACT

The present invention provides methods for radiolabeling compounds useful as Hsp90 inhibitors. The present invention also provides intermediates useful in such methods, and compositions of radiolabeled compounds. The present invention provides, among other things novel methods for the synthesis of radiolabeled compounds. In certain embodiments, the present invention provides compounds of formula I.

24 Claims, 3 Drawing Sheets

(56) References Cited

U.S. PATENT DOCUMENTS

2019/0023708 A1   1/2019   Chiosis

FOREIGN PATENT DOCUMENTS

| | | |
|---|---|---|
| WO | WO-2008/005937 A2 | 1/2008 |
| WO | WO-2011/044394 A1 | 4/2011 |
| WO | WO-2012/138894 A1 | 10/2012 |
| WO | WO-2012/138896 A1 | 10/2012 |
| WO | WO-2012/149493 A2 | 11/2012 |
| WO | WO-2013/009655 A2 | 1/2013 |
| WO | WO-2013/009657 A1 | 1/2013 |
| WO | WO-2014/144715 A1 | 9/2014 |
| WO | WO-2015/023976 A2 | 2/2015 |
| WO | WO-2016/044629 A1 | 3/2016 |
| WO | WO-2017/062520 A1 | 4/2017 |

OTHER PUBLICATIONS

International Search Report for PCT/US2014/072090, 4 pages (dated Aug. 18, 2015).
Qu, W. et al, Novel styrylpyridines as probes for SPECT imaging of amyloid plaques, J. Med. Chem., 50(9): 2157-65 (2007).
Written Opinion for PCT/US2014/072090, 9 pages (dated Aug. 18, 2015).

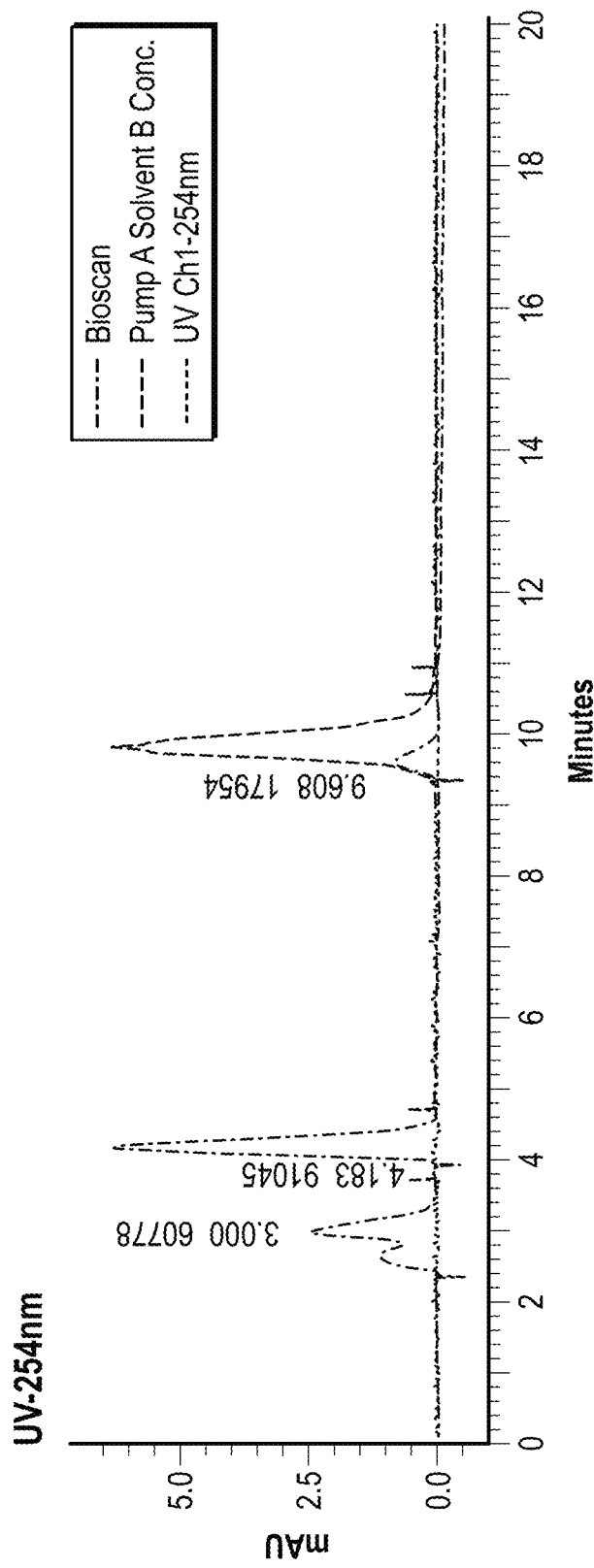

METHODS AND REAGENTS FOR RADIOLABELING

CROSS REFERENCE TO RELATED APPLICATIONS

The present invention is a divisional of U.S. application Ser. No. 15/971,908, filed May 4, 2018, now U.S. Pat. No. 10,329,293, which is a divisional of U.S. application Ser. No. 15/107,229, filed Jun. 22, 2016, now U.S. Pat. No. 9,994,573, which is a national phase of PCT/US2014/072090, filed Dec. 23, 2014, which claims priority to U.S. provisional patent application No. 61/919,901, filed Dec. 23, 2013, the entire contents of which are hereby incorporated by reference.

BACKGROUND OF THE INVENTION

Hsp90 is a family of proteins involved in many cellular functions, including the cellular defense against stress, the stability and function of mutated proteins, and the conformational maturation of key proteins involved in the growth response of cells to extracellular factors. In addition, Hsp90 has also been shown to be overexpressed in multiple tumor types and as a function of oncogenic transformation. Hsp90 inhibitors are therefore a highly pursued target in drug discovery efforts.

Radiolabeled Hsp90 inhibitors can be used clinically in a variety of applications related to treatment regimen, diagnosis, and patient monitoring. However, the currently available methods for placing a radioisotope on an Hsp90 inhibitor compound are prohibitively expensive due to poor yields and/or synthetic routes that sacrifice significant amounts of precious radioisotope.

SUMMARY OF THE INVENTION

The present invention provides, among other things, novel methods for the synthesis of radiolabelled compounds. In certain embodiments, the present invention provides compounds of formula I:

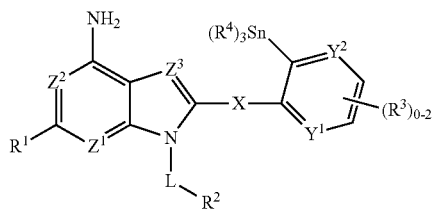

wherein each of $R^1$, $R^2$, $R^3$, $R^4$, L, X, $Y^1$, $Y^2$, $Z^1$, $Z^2$, and $Z^3$ is as defined above and described in classes and subclasses herein. In some embodiments, the present invention provides methods of using compounds of formula I to provide radiolabeled analogs.

BRIEF DESCRIPTION OF THE DRAWING

FIGS. 1A-1C depict an HPLC profile of purified [$^{131}$I]-Compound 5 (PU-H71).

DETAILED DESCRIPTION OF THE INVENTION

Figure 1A:
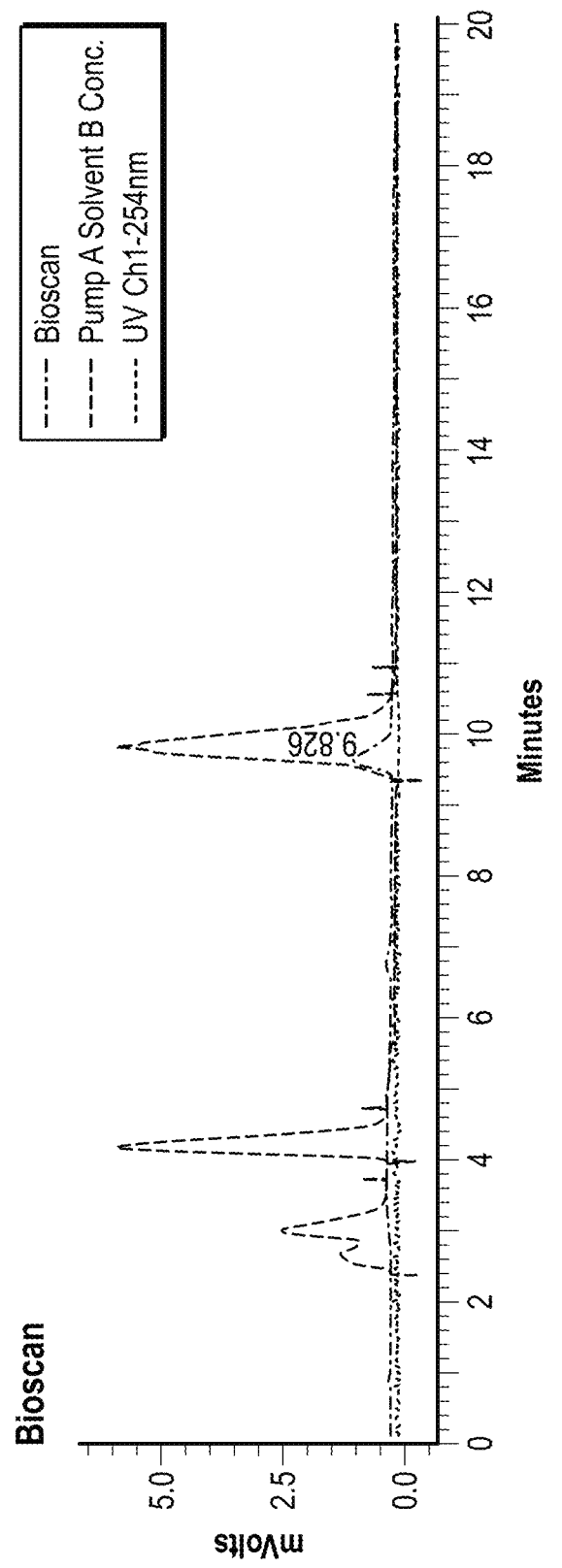
Figure 1B:
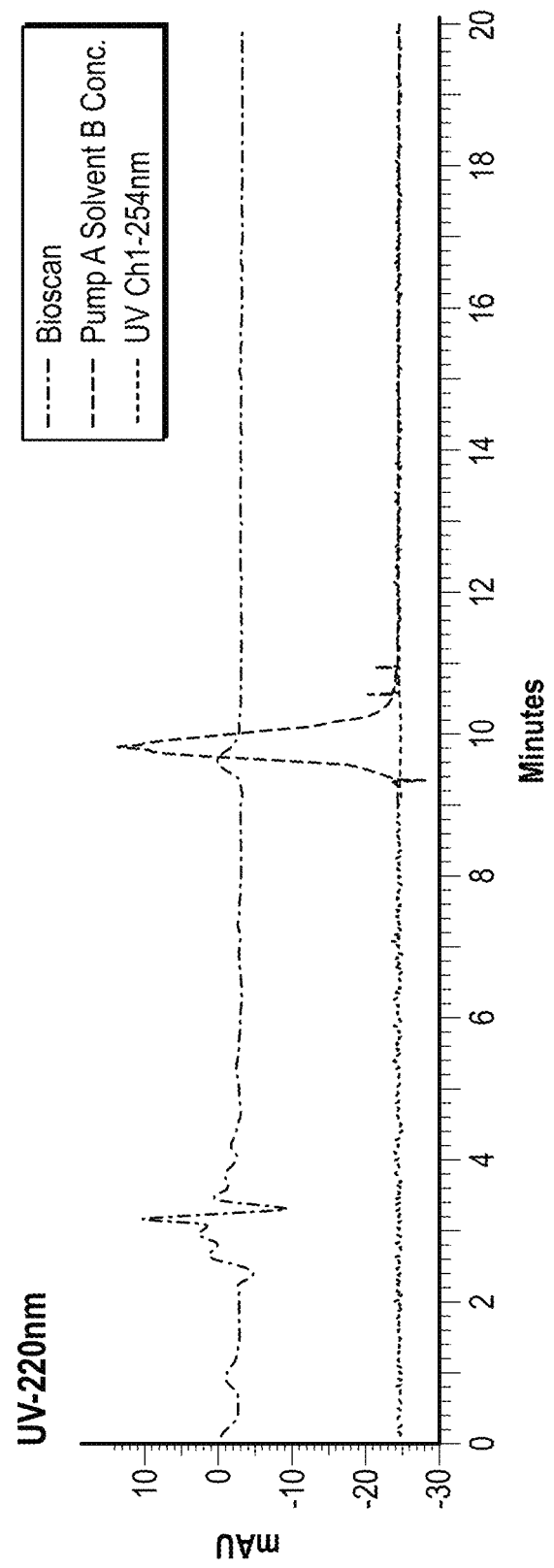

The present invention encompasses the recognition that the ability to measure particular forms of Hsp90 is advantageous to patient selection, treatment, and outcome. For example, in the cancer context, there exists an "oncogenic Hsp90" species, the abundance of which is not dictated by Hsp90 expression alone, that can be used to predict for sensitivity to Hsp90 inhibition therapy. Measuring the presence and/or abundance of this oncogenic Hsp90 in tumors is therefore a method to predict patient response to Hsp90 therapy. The use of labeled Hsp90 inhibitors facilitates measuring the abundance of oncogenic Hsp90 in a multitude of tumors and tumor cells, as demonstrated by Applicant's prior work disclosed in International Patent Publication No. WO2013/009655. However, Applicant has shown that cancer is not the only case in which the presence of various Hsp90 species is relevant. For example, neurodegenerative contexts also display a pathogenic (i.e., stress-specific) Hsp90, the relative abundance of which can be measured using labeled Hsp90 inhibitors (WO2013/009655).

One problem with the current methodologies for radiolabeling is that radioisotopes are expensive, and the loss of material during synthesis of a radiolabeled compound is very costly. In particular, poor-yielding synthesis or lackluster synthetic routes often cause the loss of significant amounts of radioisotope. However, improved synthetic routes to radiolabeled compounds can make the production of such chemical tools much more economically feasible, as demonstrated by the ensuing Examples. Thus, in some embodiments, the present invention provides the identification of a previously unknown problem, namely that the expense of synthesizing labeled compounds was detrimental to the production and availability of radiolabeled Hsp90 inhibitors in both the pre-clinical and clinical medicine.

In one particular example, the existing process for preparing radiolabeled PU-H71 (compound 5, infra) requires the use of a tin-labeled precursor that is Boc-protected (3), as shown in Scheme A, below. This intermediate 3 can provide radiolabeled PU-H71 (5) in two steps as is shown in Scheme A (steps c and d). The first step is radioiodination (step c) followed by removal of the Boc group (step d).

Scheme A

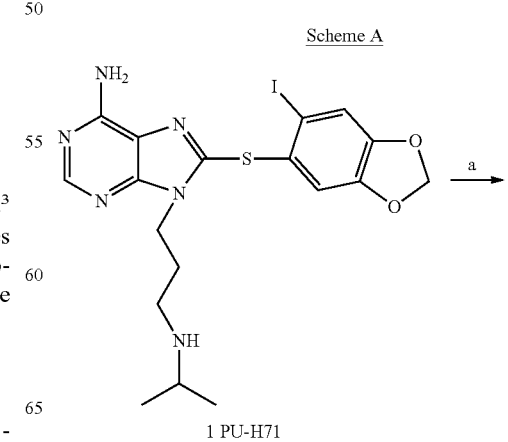

1 PU-H71

-continued

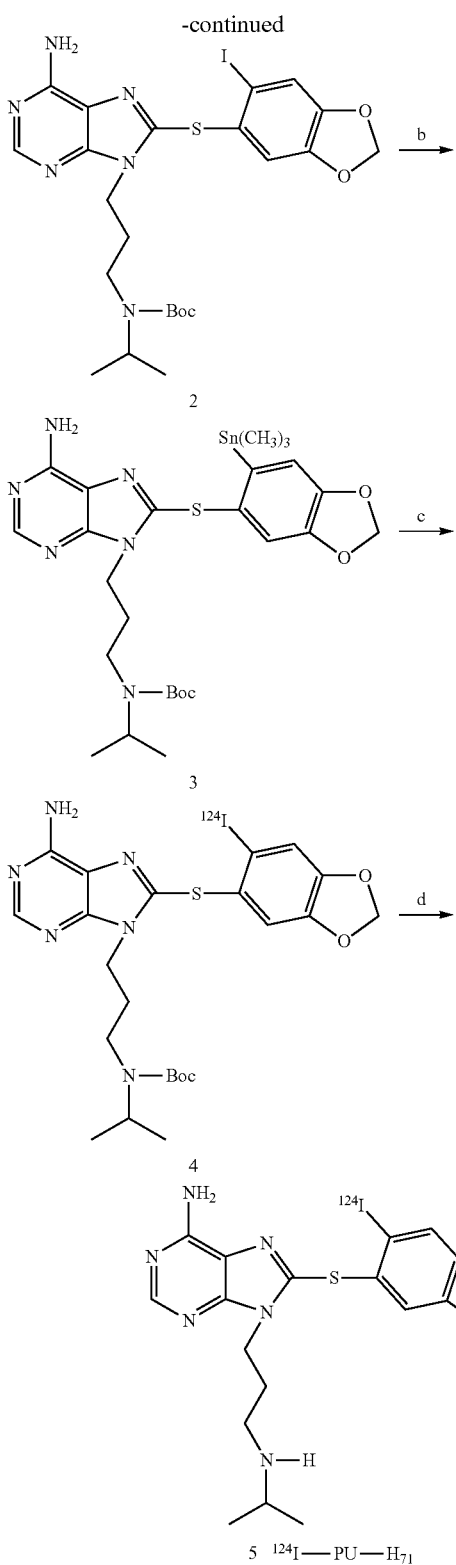

Synthesis of stannane precursor 3 and labeled compound 5. Reagents and conditions: a. Et$_3$N, (Boc)$_2$O, CH$_2$Cl$_2$, rt; b. Pd(PPh$_3$)$_4$, hexamethylditin, dioxane, 90° C.; c. 124I—NaI, chloramine-7, 50° C.; d. 6M HCl, 50° C.

Since the cost of radioactive isotopes is high, (i.e. the cost for iodine-124-250$ per mCi) any improvement in the yields is extremely useful to lower production costs. In certain embodiments, the present invention provides methods to improve the synthesis of labeled Hsp90 inhibitors by reducing the current two-step procedure to a single step by removing the second step in the current process (i.e., step d). In addition to producing more consistent results, provided methods have higher typical isolated yields and require less radiochemistry time, resulting in significant cost savings per dose of radiolabeled compound. Such methods and others are described below in the ensuing description and Examples.

In certain embodiments, the present invention provides a compound of formula I:

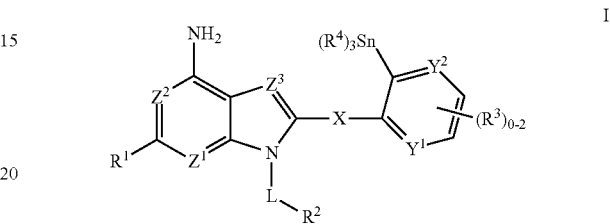

wherein:
X is —CH$_2$—, —O—, or —S—;
Y$^1$ and Y$^2$ are independently —CR$^{3a}$— or —N—;
Z$^1$, Z$^2$, and Z$^3$ are independently —CH— or —N—;
R$^1$ is hydrogen or halogen;
L is a straight or branched, optionally substituted C$_{2-14}$ aliphatic group wherein one or more carbons are optionally and independently replaced by -Cy-, —NR—, —N(R)C(O)—, —C(O)N(R)—, —C(O)N(O)—, —N(R)SO$_2$—, —SO$_2$N(R)—, —O—, —C(O)—, —OC(O)—, —C(O)O—, —S—, —SO—, or —SO$_2$—,
each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
R$^2$ is hydrogen or an optionally substituted group selected from the group consisting of C$_{1-6}$ aliphatic, phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic carbocyclyl, 7- to 10-membered saturated or partially unsaturated bicyclic heterocyclyl having 1-4 heteroatoms selected from oxygen, nitrogen, or sulfur, 7- to 10-membered bicyclic heteroaryl having 1-4 heteroatoms selected from oxygen, nitrogen, or sulfur, or 8- to 10-membered bicyclic aryl;
each R$^3$ is independently, halogen, —NO$_2$, —CN, —OR, —SR, —N(R)$_2$, —C(O)R, —CO$_2$R, —C(O)C(O)R, —C(O)CH$_2$C(O)R, —S(O)R, —S(O)$_2$R, —C(O)N(R)$_2$, —SO$_2$N(R)$_2$, —OC(O)R, —N(R)C(O)R, —N(R)N(R)$_2$, or optionally substituted C$_{1-6}$ aliphatic or pyrrolyl; or
two R$^3$ groups are taken together with their intervening atoms to form Ring A, wherein Ring A is a 3- to 7-membered partially unsaturated carbocyclyl, phenyl, a 5- to 6-membered partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, or 6-membered aryl;

$R^{3a}$ is $R^3$ or hydrogen;

$R^4$ is $C_{1-4}$ alkyl;

each R is independently hydrogen or an optionally substituted group selected from $C_{1-6}$ aliphatic, phenyl, 3- to 7-membered saturated or partially unsaturated carbocyclyl, 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur, or:

two R groups on the same nitrogen are taken together with their intervening atoms to form an optionally substituted ring selected from 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur.

Definitions

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001, the entire contents of which are hereby incorporated by reference.

The abbreviations used herein have their conventional meaning within the chemical and biological arts. The chemical structures and formulae set forth herein are constructed according to the standard rules of chemical valency known in the chemical arts.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In some embodiments, aliphatic groups contain 1-4 aliphatic carbon atoms. In some embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic and bicyclic ring systems having a total of five to 10 ring members, wherein at least one ring in the system is aromatic and wherein each ring in the system contains three to seven ring members. The term "aryl" may be used interchangeably with the term "aryl ring". In some embodiments, an 8-10 membered bicyclic aryl group is an optionally substituted naphthyl ring. In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may, when specified, contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R, —O—(CH$_2$)$_{0-4}$C(O)OR; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, -(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet$$_2$, or —NO$_2$, wherein each R$^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^†$, —$NR^†_2$, —$C(O)R^†$, —$C(O)OR^†$, —$C(O)C(O)R^†$, —$C(O)CH_2C(O)R^†$, —$S(O)_2R^†$, —$S(O)_2NR^†_2$, —$C(S)NR^†_2$, —$C(NH)NR^†_2$, or —$N(R^†)S(O)_2R^†$; wherein each $R^†$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^†$ are independently halogen, —$R^●$, -(halo$R^●$), —OH, —$OR^●$, —$O(haloR^●)$, —CN, —C(O)OH, —$C(O)OR^●$, —$NH_2$, —$NHR^●$, —$NR^●_2$, or —$NO_2$, wherein each $R^●$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference.

In certain embodiments, the neutral forms of the compounds are regenerated by contacting the salt with a base or acid and isolating the parent compound in the conventional manner. In some embodiments, the parent form of the compound differs from the various salt forms in certain physical properties, such as solubility in polar solvents.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention.

The term "oxo," as used herein, means an oxygen that is double bonded to a carbon atom, thereby forming a carbonyl.

One of ordinary skill in the art will appreciate that the synthetic methods, as described herein, utilize a variety of protecting groups. By the term "protecting group," as used herein, it is meant that a particular functional moiety, e.g., O, S, or N, is masked or blocked, permitting, if desired, a reaction to be carried out selectively at another reactive site in a multifunctional compound. Suitable protecting groups are well known in the art and include those described in detail in *Protecting Groups in Organic Synthesis*, T. W. Greene and P. G. M. Wuts, $3^{rd}$ edition, John Wiley & Sons, 1999, the entirety of which is incorporated herein by reference. In certain embodiments, a protecting group reacts selectively in good yield to give a protected substrate that is stable to the projected reactions; the protecting group is preferably selectively removable by readily available, preferably non-toxic reagents that do not attack the other functional groups; the protecting group forms a separable derivative (more preferably without the generation of new stereogenic centers); and the protecting group will preferably have a minimum of additional functionality to avoid further sites of reaction. As detailed herein, oxygen, sulfur, nitrogen, and carbon protecting groups may be utilized. Amino-protecting groups include methyl carbamate, 9-fluorenylmethyl carbamate (Fmoc), 9-(2,7-dibromo)fluoroenylmethyl carbamate, 4-methoxyphenacyl carbamate (Phenoc), 2,2,2-trichloroethyl carbamate (Troc), 2-trimethylsilylethyl carbamate (Teoc), 1-methyl-1-(4-biphenylyl)ethyl carbamate (Bpoc), 2-(2'- and 4'-pyridyl)ethyl carbamate (Pyoc), 2-(N,N-dicyclohexylcarboxamido)ethyl carbamate, t-butyl carbamate (BOC), allyl carbamate (Alloc), 4-nitrocinnamyl carbamate (Noc), N-hydroxypiperidinyl carbamate, alkyldithio carbamate, benzyl carbamate (Cbz), p-nitrobenzyl carbamate, p-chlorobenzyl carbamate, diphenylmethyl carbamate, 2-methylsulfonylethyl carbamate, 2-(p-toluenesulfonyl)ethyl carbamate, 2,4-dimethylthiophenyl carbamate (Bmpc), 2-triphenylphosphonioisopropyl carbamate (Ppoc), m-chloro-p-acyloxybenzyl carbamate, p-(dihydroxyboryl)benzyl carbamate, m-nitrophenyl carbamate, 3,5-dimethoxybenzyl carbamate, o-nitrobenzyl carbamate, phenyl(o-nitrophenyl)methyl carbamate, N'-p-toluenesulfonylaminocarbonyl derivative, N'-phenylaminothiocarbonyl derivative, t-amyl carbamate, p-cyanobenzyl carbamate, cyclohexyl carbamate, cyclopentyl carbamate, p-decyloxybenzyl carbamate, 2,2-dimethoxycarbonylvinyl carbamate, 2-furanylmethyl carbamate, isobornyl carbamate, isobutyl carbamate, 1-methyl-1-phenylethyl carbamate, 1-methyl-1-(4-pyridyl)ethyl carbamate, phenyl carbamate, formamide, acetamide, chloroacetamide, trichloroacetamide, trifluoroacetamide, phenylacetamide, 3-phenylpropanamide, picolinamide, N-benzoylphenylalanyl derivative, benzamide, p-phenylbenzamide, o-nitrophenoxyacetamide, acetoacetamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-2,5-dimethylpyrrole, N-methylamine, N-allylamine, N-[2-(trimethylsilyl)ethoxy]methylamine (SEM), N-3-acetoxypropylamine, N-benzylamine, N-triphenylmethylamine (Tr), N-2-picolylamino N'-oxide, N-1,1-dimethylthiomethyleneamine, N-benzylideneamine, N-p-methoxybenzylideneamine, N—(N',N'-dimethylaminomethylene)amine, N,N'-isopropylidenediamine, N-p-nitrobenzylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-nitroamine, N-nitrosoamine, amine N-oxide, diphenylphosphinamide (Dpp), dimethylthiophosphinamide (Mpt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), methanesulfonamide (Ms), β-trimethylsilylethanesulfonamide (SES), benzylsulfonamide, trifluoromethylsulfonamide, and phenacylsulfonamide Exemplary protecting groups are detailed herein, however, it will be appreciated that the present invention is not intended to be limited to these protecting groups; rather, a variety of additional equivalent protecting groups can be readily identified using the above criteria and utilized in the method of the present invention. Additionally, a variety of protecting groups are described by Greene and Wuts (supra).

The term "radiolabel", as used herein, refers to a moiety comprising a radioactive isotope of at least one element. Exemplary suitable radiolabels include but are not limited to those described herein. In some embodiments, a radiolabel is one used in positron emission tomography (PET). In some embodiments, a radiolabel is one used in single-photon emission computed tomography (SPECT).

The symbol "⌇", except when used as a bond to depict unknown or mixed stereochemistry, denotes the point of attachment of a chemical moiety to the remainder of a molecule or chemical formula.

Compounds

As described above, in certain embodiments the present invention provides a compound of formula I:

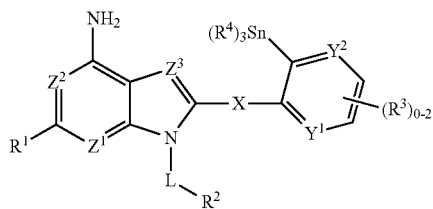

I wherein each of $R^1$, $R^2$, $R^3$, $R^4$, L, X, $Y^1$, $Y^2$, $Z^1$, $Z^2$, and $Z^3$ is as defined above and described in classes and subclasses herein.

In some embodiments, X is —$CH_2$—. In some embodiments, X is —S—. In other embodiments, X is —O—.

In certain embodiments, $Y^1$ is —$CR^{3a}$—. In certain embodiments, $Y^1$ is —N—.

In certain embodiments, $Y^2$ is —$CR^{3a}$—. In certain embodiments, $Y^2$ is —N—.

In some embodiments, $R^{3a}$ is hydrogen.

In certain embodiments, $Z^1$ is —CH—. In certain embodiments, $Z^1$ is —N—.

In certain embodiments, $Z^2$ is —CH—. In certain embodiments, $Z^2$ is —N—.

In certain embodiments, $Z^3$ is —CH—. In certain embodiments, $Z^3$ is —N—.

In some embodiments, $R^1$ is hydrogen. In some embodiments, $R^1$ is halogen. In some embodiments, $R^1$ is fluro.

In some embodiments, -L-$R^2$ comprises a methylene that is replaced with —NH— to form a secondary amine.

In some embodiments, L is a straight or branched, $C_{2-14}$ aliphatic group wherein one or more carbons are independently replaced by —NR—, wherein R is other than a -Boc protecting group. In some embodiments, -L-$R^2$ does not contain a Boc-protected secondary amine. In some embodiments, -L-$R^2$ does not contain a secondary amine that is protected with an acid-labile protecting group. In some embodiments, -L-$R^2$ does not contain a protected secondary amine.

In some embodiments, L is a straight or branched, optionally substituted $C_{2-14}$ aliphatic group wherein one, two, or three carbons are optionally and independently replaced by -Cy-, —NR—, —N(R)C(O)—, —C(O)N(R)—, —C(O)N(O)—, —N(R)$SO_2$—, —$SO_2$N(R)—, —O—, —C(O)—, —OC(O)—, —C(O)O—, —S—, —SO—, or —$SO_2$—, In some embodiments, L is a straight or branched, $C_{2-14}$ aliphatic group wherein a methylene of the aliphatic group is replaced with —NH— to form a secondary amine. In some embodiments, L is a straight or branched, $C_{2-12}$ aliphatic group wherein a methylene of the aliphatic group is replaced with —NH— to form a secondary amine. In some embodiments, L is a straight or branched, $C_{2-10}$ aliphatic group wherein a methylene of the aliphatic group is replaced with —NH— to form a secondary amine. In some embodiments, L is a straight or branched, $C_{2-8}$ aliphatic group wherein a methylene of the aliphatic group is replaced with —NH— to form a secondary amine. In some embodiments, L is a straight or branched, $C_{2-6}$ aliphatic group wherein a methylene of the aliphatic group is replaced with —NH— to form a secondary amine. In some embodiments, L is a straight or branched, $C_{2-4}$ aliphatic group wherein a methylene of the aliphatic group is replaced with —NH— to form a secondary amine. In some embodiments, L is a straight or branched, $C_{6-14}$ aliphatic group wherein a methylene of the aliphatic group is replaced with —NH— to form a secondary amine. In some embodiments, L is a straight or branched, $C_{6-12}$ aliphatic group wherein a methylene of the aliphatic group is replaced with —NH— to form a secondary amine.

In some embodiments, L is a straight or branched, $C_{2-14}$ aliphatic group wherein one or more carbons are optionally and independently replaced by -Cy- or —C(O)—. In some embodiments, L is a straight or branched, $C_{2-8}$ aliphatic group wherein one or more carbons are optionally and independently replaced by -Cy- or —C(O)—. In certain embodiments, L is a straight or branched, $C_{2-8}$ aliphatic group wherein one carbon of L is replaced by -Cy- and wherein -Cy- is a 6-membered saturated ring having one heteroatom selected from nitrogen.

In some embodiments, -Cy- is an optionally substituted 3-8 membered bivalent, saturated, partially unsaturated, or aryl ring having 0-4 heteroatoms independently selected from nitrogen, oxygen, or sulfur. In some embodiments, -Cy- is an optionally substituted 3-8 membered bivalent, saturated ring having 1-2 heteroatoms independently selected from nitrogen, oxygen, or sulfur. In some embodiments, -Cy- is an optionally substituted 5-6 membered bivalent, saturated ring having 1-2 heteroatoms independently selected from nitrogen, oxygen, or sulfur. In some embodiments, -Cy- is bivalent piperidinyl.

In some embodiments, $R^2$ is hydrogen. In other embodiments, $R^2$ is optionally substituted $C_{1-6}$ aliphatic. In some embodiments, $R^2$ is optionally substituted $C_{1-4}$ aliphatic. In some embodiments, $R^2$ is $C_{1-4}$ alkyl.

In some embodiments, $R^2$ is 3- to 7-membered saturated or partially unsaturated monocyclic heterocyclyl having 1-2 heteroatoms selected from oxygen, nitrogen, or sulfur. In some embodiments, $R^2$ is 5- to 6-membered saturated or partially unsaturated monocyclic heterocyclyl having 1-2 heteroatoms selected from oxygen, nitrogen, or sulfur. In some embodiments, $R^2$ is piperidinyl. In some embodiments, $R^2$ is aziridinyl.

In some embodiments, $R^2$ is 3- to 7-membered saturated or partially unsaturated monocyclic carbocyclyl. In some embodiments, $R^2$ is cyclopropyl.

In some embodiments, -L-$R^2$ forms a primary aminoalkyl group. In some embodiments, -L-$R^2$ forms a secondary alkyl-amino-alkyl group.

In some embodiments, -L-$R^2$ is selected from the following:

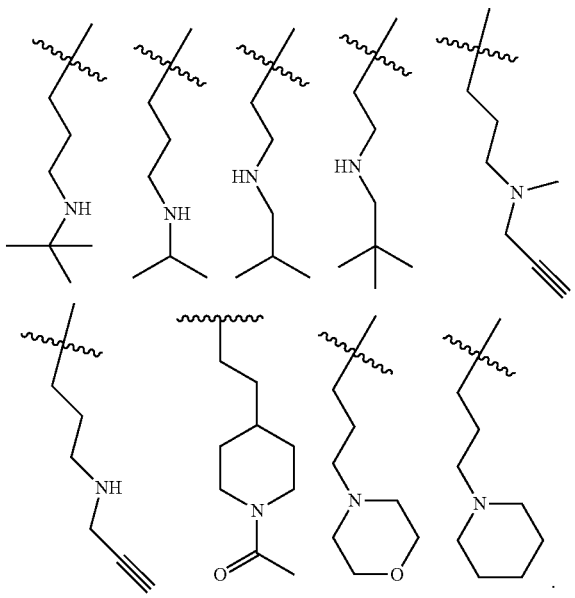

In some embodiments, -L-$R^2$ is selected from the following:

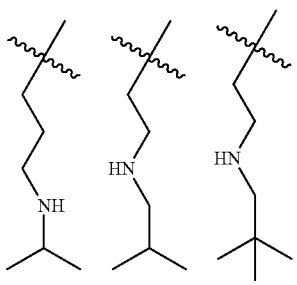

In some embodiments, each $R^3$ is independently halogen, —CN, —OR, —SR, —N(R)$_2$, or optionally substituted $C_{1-6}$ aliphatic. In some embodiments, each $R^3$ is —OR. In some embodiments, one or both of $Y^1$ and $Y^2$ is —CR$^{3a}$— and there are two occurrences of $R^3$. In some embodiments, one or both of $Y^1$ and $Y^2$ is —CR$^{3a}$— and there is one occurrence of $R^3$. In some embodiments, both $Y^1$ and $Y^2$ are —N— and there are two occurrences of $R^3$. In some embodiments, both $Y^1$ and $Y^2$ are —N— and there is one occurrence of $R^3$.

In some embodiments, there is at least one substituent on the ring bearing a trialkyltin group, and one of such substituents is located at the 5' position, wherein the ring numbering is as depicted below:

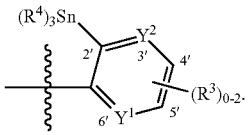

In some embodiments, there are two substituents on the ring bearing the trialkyltin group, located at the 4' and 5' positions. In some embodiments, these two substituents are taken together with their intervening atoms to form Ring A.

In certain embodiments wherein $R^3$ is —OR, R is $C_{1-6}$ aliphatic. In certain embodiments wherein $R^3$ is —OR, R is methyl.

In some embodiments, two $R^3$ groups are taken together with their intervening atoms to form Ring A, wherein Ring A is a 5- to 6-membered partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, or 6-membered aryl. In certain embodiments, Ring A is a 5-membered partially unsaturated monocyclic heterocyclyl having 2 heteroatoms selected from oxygen. In certain embodiments, Ring A is a 5-membered partially unsaturated monocyclic heterocyclyl having 1 heteroatom selected from oxygen. In certain embodiments, Ring A is a 6-membered partially unsaturated monocyclic heterocyclyl having 2 heteroatoms selected from oxygen. In some embodiments, Ring A is phenyl.

In some embodiments, two $R^3$ groups are taken together with their intervening atoms to form Ring A, wherein Ring A is 3- to 7-membered partially unsaturated carbocyclyl. In some embodiments, Ring A is 5- to 6-membered partially unsaturated carbocyclyl.

In some embodiments, $R^4$ is methyl. In some embodiments, $R^4$ is ethyl. In some embodiments, $R^4$ is butyl.

In certain embodiments, a compound of the present invention is other than:

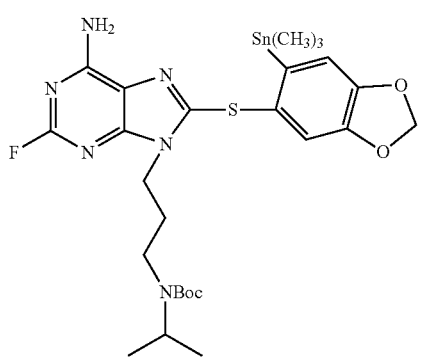

In certain embodiments, a provided compound is of formula I-a-1:

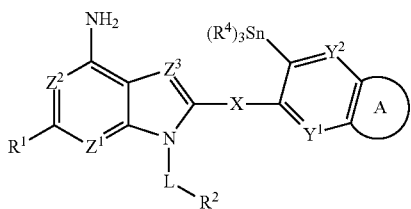
I-a-1 wherein each of Ring A, $R^1$, $R^2$, $R^4$, L, $Y^1$, $Y^2$, $Z^1$, $Z^2$, $Z^3$, and X is as defined above and described in classes and subclasses herein, both singly and in combination.

In some embodiments, a provided compound is of formula I-a:

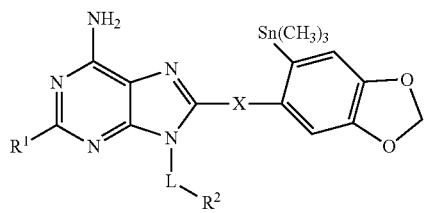
I-a wherein each of $R^1$, $R^2$, L, and X is as defined above and described in classes and subclasses herein, both singly and in combination. In certain embodiments, a compound is of formula I-a and:

X is —CH$_2$— or —S—;

$R^1$ is hydrogen or halogen; and

L is a straight or branched, C$_{2-14}$ aliphatic group wherein one or more carbons are independently replaced by —NR—, wherein R is other than a -Boc protecting group.

In some embodiments, a provided compound is of formula I-b, I-c, I-d, I-e, I-f, I-g, I-h, or I-j:

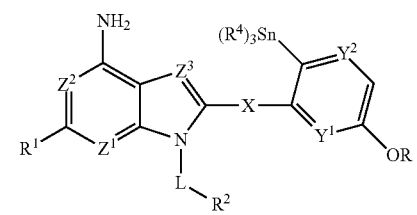
I-b

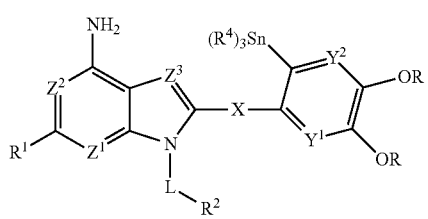
I-c

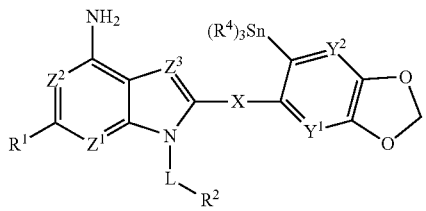
I-d

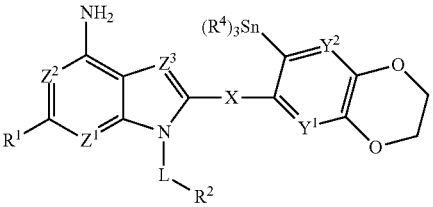
I-e

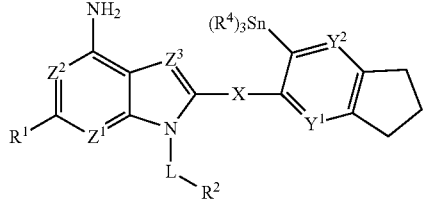
I-f

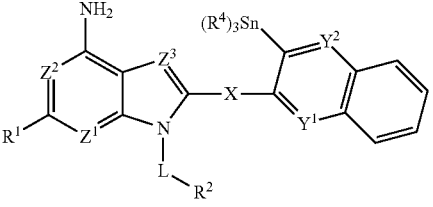
I-g

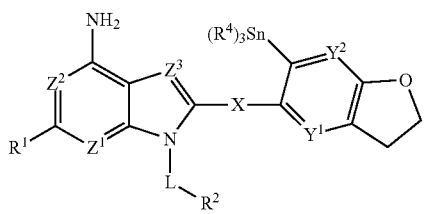
I-h

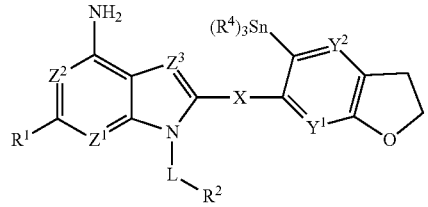
I-j wherein each of $R^1$, $R^2$, $R^4$, L, X, $Y^1$, $Y^2$, $Z^1$, $Z^2$, $Z^3$, and R is as defined above and described in classes and subclasses herein, both singly and in combination.

In some embodiments, a provided compound is of formula I-i:

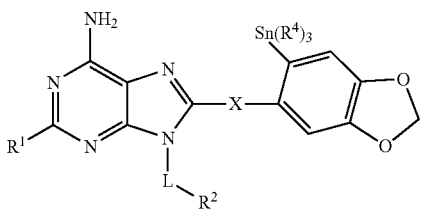

wherein each of R¹, R², R⁴, L, and X is as defined above and described in classes and subclasses herein, both singly and in combination.

In certain embodiments, a compound of formula I is selected from those depicted in Table 1.

TABLE 1

Exemplary compounds of Formula I

I-1

I-2

I-3

TABLE 1-continued

Exemplary compounds of Formula I

I-4

I-5

Synthesis of Compounds

Compounds of the invention may be synthesized according to the schemes described below. The reagents and conditions described are intended to be exemplary and not limiting. As one of skill in the art would appreciate, various analogs may be prepared by modifying the synthetic reactions such as using different starting materials, different reagents, and different reaction conditions (e.g., temperature, solvent, concentration, etc.)

It will be appreciated that any intermediate depicted Schemes A, B, or C may be isolated and/or purified prior to each subsequent step. Alternatively, any intermediate depicted in Schemes A, B, or C may be utilized in subsequent steps without isolation and/or purification. Such telescoping of steps is contemplated in the present invention.

In some embodiments, compounds described herein may be purified by any means known in the art. In some embodiments, purification of a compound described herein comprises filtration, chromatography, distillation, crystallization, or a combination thereof. In some embodiments, chromatography comprises high performance liquid chromatography (HPLC). In some embodiments, chromatography comprises normal phase, reverse phase, or ion-exchange elution over a cartridge comprising suitable sorbent media. Purification via chromatography methods typically utilizes one or more solvents, which are known to the skilled artisan or determined by routine experimentation. In some embodiments, chromatography comprises HPLC using an elution solvent comprising acetonitrile. In some embodiments, chromatography comprises HPLC using an elution solvent comprising ethanol. In some embodiments, compound 5 is purified by any of the methods described in this paragraph.

In one aspect, the present invention provides methods for the synthesis of compounds of formula I and I$^L$ and intermediates thereto. In some embodiments, such methods are as shown in Scheme B, below:

Scheme B

Method 1

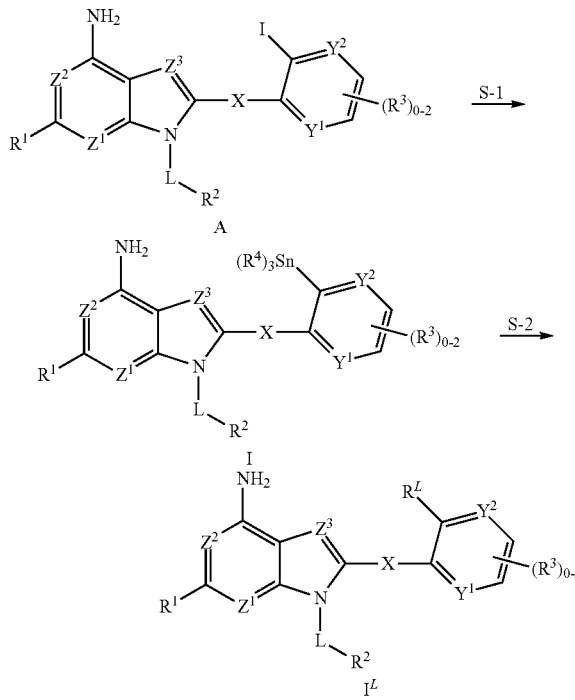

wherein $R^L$ is a radiolabel and each of $R^1$, $R^2$, $R^3$, $R^4$, L, $R^L$, X, $Y^1$, $Y^2$, $Z^1$, $Z^2$, $Z^3$ is as defined herein and described in classes and subclasses herein, both singly and in combination.

Compounds of formula A are known in the art and the skilled artisan will be familiar with methods of making such compounds. Exemplary syntheses of compounds of formula A are described in International Patent Application Publications WO/2008/005937, WO/2006/084030, WO/2007/134298, WO/2011/044394, WO/2012/138894, and WO/2012/138896, U.S. Pat. No. 8,586,605, and U.S. Patent Publication Nos. US/20100016586 and US/20100292255, the entire contents of each of which are hereby incorporated by reference herein.

At step S-1, aryl iodide A is reacted under suitable conditions to provide a trialkyltin compound of formula I. Suitable conditions for the installation of a trimethyltin group from an aryl iodide are known in the art and contemplated by the present disclosure, including those described in International Patent Application Publication Nos. WO2006084030 and WO2013009655 and US Patent Application Publication No. US2011312980. Suitable conditions for the installation of a tributyltin group from an aryl iodide are also known in the art (see, for example Qu et al., *J. Med. Chem.* 2007, 50, 2157-65; Farina, V.; Krishnamurthy, V.; Scott, W. J. The Stille reaction. *Org. React.* (Hoboken, N.J., U.S.) 1997, 50) and contemplated by the present disclosure. However, unlike prior methods, step S-1 does not employ a protecting group on a secondary amine of L-$R^2$, if such secondary amine is present. In some embodiments, suitable conditions comprise a catalyst. In some embodiments, a catalyst is a palladium catalyst. In certain embodiments, a catalyst is $Pd(PPh_3)_4$. In some embodiments, a catalyst is $PdCl_2(CH_3CN)_2$. In some embodiments, a catalyst is $Pd(PPh_3)_2Br_2$.

In certain embodiments, step S-1 employs a suitable solvent. Examples of solvents suitable for use at step S-1 include polar solvents (e.g., ethers, DMF), aromatic hydrocarbons (e.g., toluene), or combinations thereof. In some embodiments, a solvent is or comprises dioxane or THF (tetrahydrofuran). In some embodiments, a solvent is or comprises dioxane. In some embodiments, a solvent is or comprises DMF. In some embodiments, a solvent is or comprises toluene.

In some embodiments, step S-1 is carried out at temperatures of about 25-150° C. In some embodiments, the temperature is about 60-110° C. In some embodiments, the temperature is about 90° C.

In certain embodiments, the present invention provides a method comprising the steps of:

a) providing an aryl iodide compound of formula A:

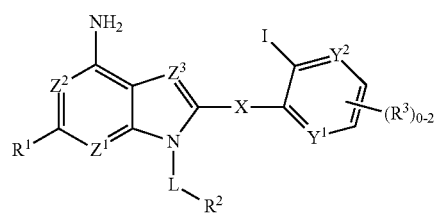

wherein each of $R^1$, $R^2$, $R^3$, L, $Y^1$, $Y^2$, $Z^1$, $Z^2$, $Z^3$, and X is as defined above and described in classes and subclasses herein, both singly and in combination; and b) reacting the aryl iodide of formula A under suitable conditions to provide a trialkyltin compound of formula I:

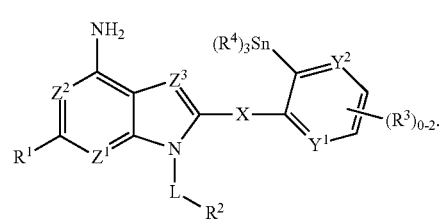

wherein $R^4$ is as defined above and described in classes and subclasses herein, both singly and in combination.

At step S-2, a compound of formula I may be converted to radiolabeled compound $I^L$. Suitable conditions for the installation of a radiolabel from a trialkyltin are known in the art and contemplated by the present disclosure, including those described in International Patent Application Publication Nos. WO2006084030 and WO2013009655 and US Patent Application Publication No. US2011312980. However, unlike prior methods, step S-2 does not employ a protecting group on a secondary amine of L-$R^2$, if such secondary amine is present. In some embodiments, suitable methods comprise mixing a radiolabel reagent with a compound of formula I optionally in a suitable solvent. In some embodiments, a radiolabel reagent is [$^{131}$I]—NaI solution.

In some embodiments, the present invention provide a method comprising the steps of:

a) providing a trialkyltin compound of formula I:

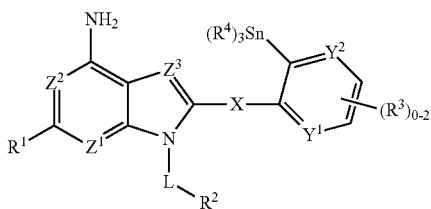

wherein each of $R^1$, $R^2$, $R^3$, $R^4$, L, $Y^1$, $Y^2$, $Z^1$, $Z^2$, $Z^3$, and X is as defined above and described in classes and subclasses herein, both singly and in combination; and b) reacting the trialkyltin compound of formula I under suitable conditions to provide a compound of formula $I^L$:

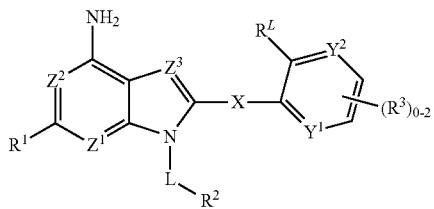

wherein $R^L$ is a radiolabel.

In certain embodiments, $R^L$ is or comprises an atom selected from the group consisting of $^{131}I$, $^{125}I$, $^{124}I$, $^{123}I$, $^{11}C$, $^{15}O$, $^{13}N$, $^{19}F$ and $^{18}F$. In some embodiments, $R^L$ is $^{124}I$.

In some embodiments, provided methods of synthesis are as shown in Scheme C, below:

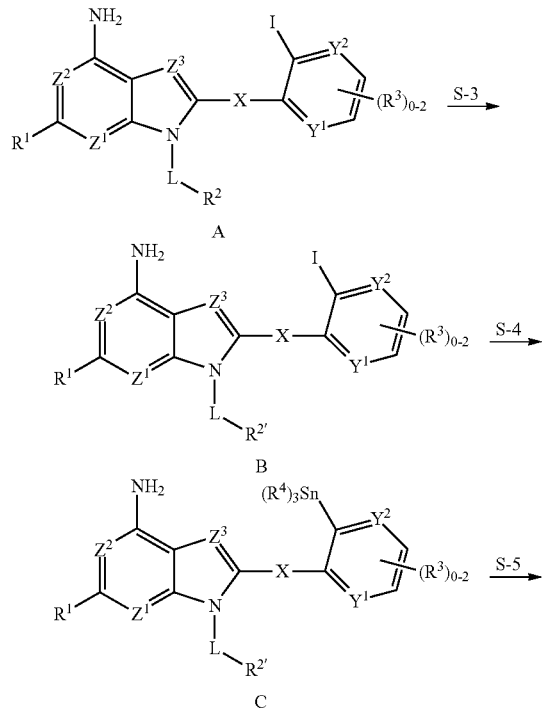

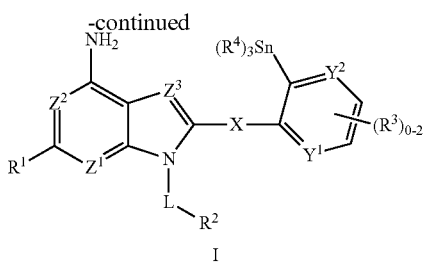

wherein:
L-$R^{2'}$ comprises a methylene that is replaced with —NH— to form a secondary amine, and wherein the secondary amine is protected with a suitable protecting group; and each of $R^1$, $R^2$, $R^3$, $R^4$, L, $Y^1$, $Y^2$, $Z^1$, $Z^2$, $Z^3$, and X is as defined above and described in classes and subclasses herein, both singly and in combination.

At step S-3, aryl iodide A is reacted under suitable protecting group conditions to provide an aryl iodide of formula B, wherein the secondary amine of $R^2$ is protected with a suitable protecting group to form $R^{2'}$. Suitable amino protecting groups are well known in the art and include those described in detail in Greene (supra). Suitable mono-protected amines include, but are not limited to, aralkylamines, carbamates, allyl amines, amides, and the like. Examples of suitable mono-protected amino moieties include t-butyloxy-carbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. In certain embodiments, a suitable protecting group is capable of being removed under mildly basic conditions. In certain embodiments, a suitable protecting group is capable of being removed under mild conditions with an amine base. In some embodiments, a suitable protecting group is Fmoc. In certain embodiments, a suitable protecting group is not one removed under acidic conditions. In some embodiments, a suitable protecting group is other than a t-butyloxycarbonyl (Boc) group.

In some embodiments, the present invention provides a method comprising the steps of:

a) providing an aryl iodide of formula A:

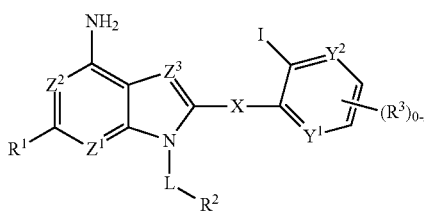

wherein each of $R^1$, $R^2$, $R^3$, L, $Y^1$, $Y^2$, $Z^1$, $Z^2$, $Z^3$, and X is as defined above and described in classes and subclasses herein, both singly and in combination; and b) reacting the aryl iodide of formula A under suitable reaction conditions to provide an aryl iodide compound of formula B:

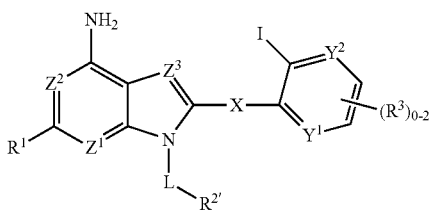

wherein R$^{2'}$ is as defined above and described in classes and subclasses herein, both singly and in combination.

At step S-4, aryl iodide of formula B is reacted under suitable conditions to provide a protected amine compound of formula C. Suitable conditions for the installation of a trialkyltin group (e.g., trimethyltin, tributyltin, etc.) from an aryl iodide are known in the art and contemplated by the present disclosure. In some embodiments, suitable conditions comprise a catalyst. In some embodiments, a catalyst is a palladium catalyst. In certain embodiments, a catalyst is Pd(PPh$_3$)$_4$. In some embodiments, a catalyst is PdCl$_2$(CH$_3$CN)$_2$. In some embodiments, a catalyst is Pd(PPh$_3$)$_2$Br$_2$.

In certain embodiments, step S-4 employs a suitable solvent. Examples of solvents suitable for use at step S-4 include polar solvents (e.g., ethers, DMF), aromatic hydrocarbons (e.g., toluene), or combinations thereof. In some embodiments, a solvent is or comprises dioxane or THF (tetrahydrofuran). In some embodiments, a solvent is or comprises dioxane. In some embodiments, a solvent is or comprises DMF. In some embodiments, a solvent is or comprises toluene.

In some embodiments, step S-4 is carried out at temperatures of about 25-150° C. In some embodiments, the temperature is about 60-110° C. In some embodiments, the temperature is about 90° C.

In certain embodiments, the present invention provides a method comprising the steps of:

a) providing an aryl iodide compound of formula B:

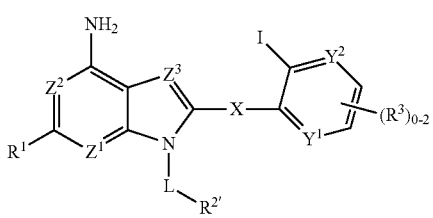

wherein each of R$^1$, R$^{2'}$, R$^3$, L, Y$^1$, Y$^2$, Z$^1$, Z$^2$, Z$^3$, and X is as defined above and described in classes and subclasses herein, both singly and in combination; and b) reacting the aryl iodide of formula B under suitable conditions to provide protected amine compound of formula C:

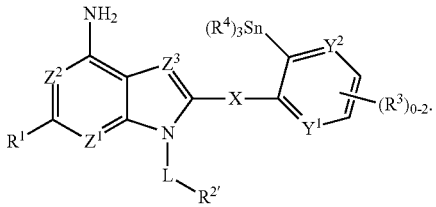

wherein R$^4$ is as defined above and described in classes and subclasses herein, both singly and in combination.

At step S-5, protected amine compound of formula C is reacted under suitable deprotection conditions to provide trialkyltin compound of formula I. It will be appreciated that deprotection conditions will depend upon the choice of protecting group, and suitable deprotection chemistries are well known in the art and include those described in detail in Greene (supra). In some embodiments, suitable deprotection conditions are mildly basic. In some embodiments, suitable deprotection conditions comprise an amine base.

In certain embodiments, the present invention provides a method comprising the steps of:

a) providing protected amine compound of formula C:

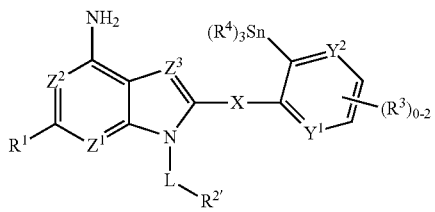

wherein each of R$^1$, R$^{2'}$, R$^3$, R$^4$, L, Y$^1$, Y$^2$, Z$^1$, Z$^2$, Z$^3$, and X is as defined above and described in classes and subclasses herein, both singly and in combination; and b) reacting the protected amine compound of formula C under suitable deprotection conditions to provide trialkyltin compound of formula I:

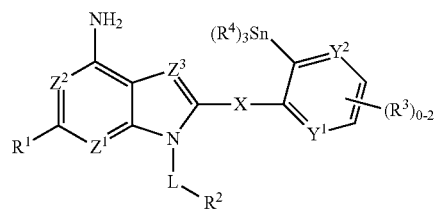

wherein R$^2$ is as defined above and described in classes and subclasses herein, both singly and in combination.

Compounds of formula I may be radiolabeled as described above for step S-2.

In certain embodiments of the above-described methods, the compound of formula I is of formula I-a-1:

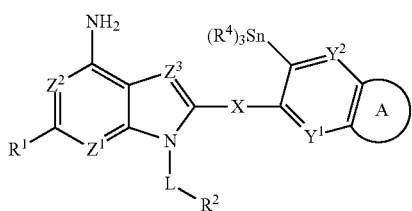
I-a-1 wherein each of Ring A, $R^1$, $R^2$, $R^4$, L, $Y^1$, $Y^2$, $Z^1$, $Z^2$, $Z^3$, and X is as defined above and described in classes and subclasses herein, both singly and in combination.

In some embodiments of the above-described methods, the compound of formula I is of formula I-a:

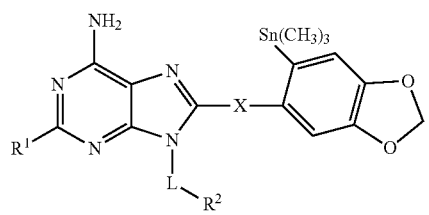
I-a wherein each of $R^1$, $R^2$, L, and X is as defined above and described in classes and subclasses herein, both singly and in combination. In certain embodiments, a compound is of formula I-a and:

X is —CH$_2$— or —S—;

$R^1$ is hydrogen or halogen; and

L is a straight or branched, C$_{2-14}$ aliphatic group wherein one or more carbons are independently replaced by —NR—, wherein R is other than a -Boc protecting group.

In some embodiments of the above-described methods, the compound of formula I is of formula I-b, I-c, I-d, I-e, I-f, I-g, I-h, or I-j:

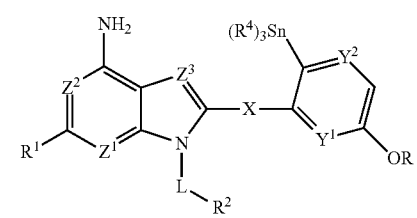
I-b

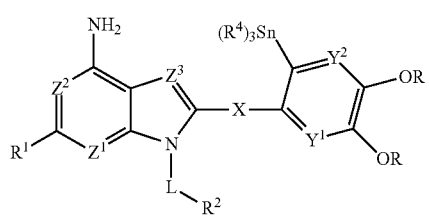
I-c

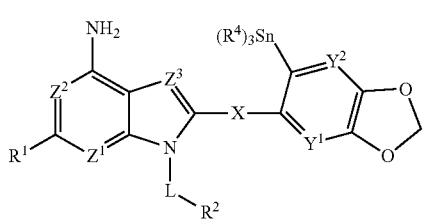
I-d

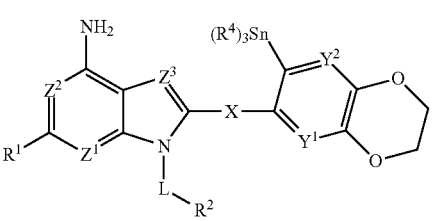
I-e

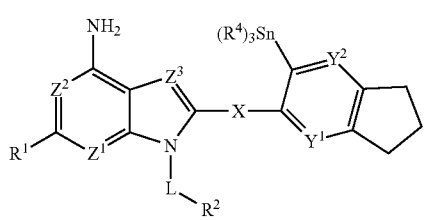
I-f

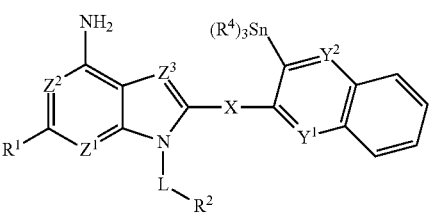
I-g

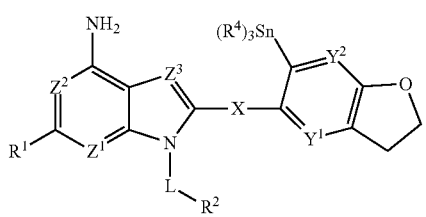
I-h

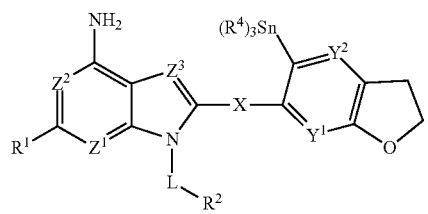
I-j wherein each of $R^1$, $R^2$, $R^4$, R, L, $Y^1$, $Y^2$, $Z^1$, $Z^2$, $Z^3$, and X is as defined above and described in classes and subclasses herein, both singly and in combination.

In certain embodiments of the above-described methods, the compound of formula I is of formula I-i:

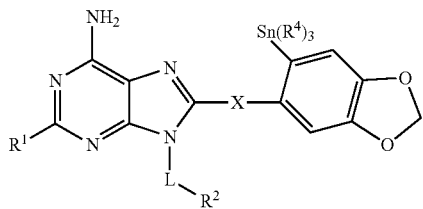

I-i wherein each of $R^1$, $R^2$, $R^4$, L, and X is as defined above and described in classes and subclasses herein, both singly and in combination.

In certain embodiments, the present invention provides a method comprising the steps of:

a) providing a trimethyltin compound:

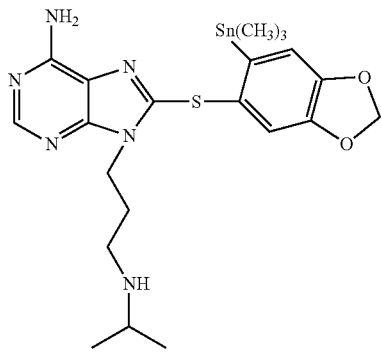

and b) reacting the trimethyltin compound under suitable conditions to provide a compound of formula I:

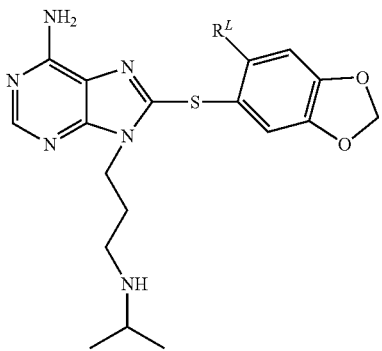 [SMILES: CC(C)NCCCn1c(Sc2cc3c(cc2I)OCO3)nc2c(N)ncnc21]

I wherein $R^L$ is a radiolabel as defined above and described in classes and subclasses herein, both singly and in combination.

In some embodiments, the present invention provides a method comprising the steps of:

a) providing an aryl iodide compound:

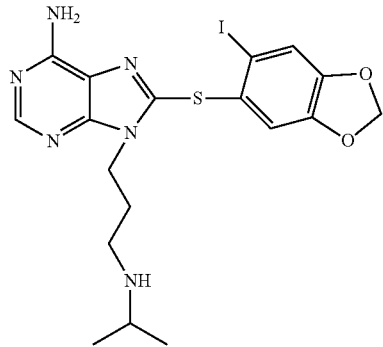

and b) reacting the aryl iodide under suitable conditions to provide a trimethyltin compound:

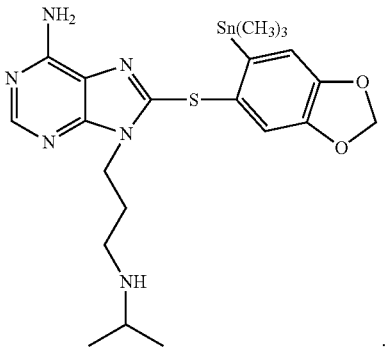

In certain embodiments, the present invention provides a method comprising the steps of:

a) providing protected amine compound:

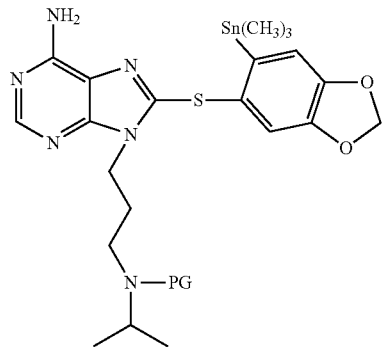

wherein PG is a suitable protecting group as defined above and described in classes and subclasses herein;

and b) reacting the protected amine compound under suitable deprotection conditions to provide trimethyltin compound:

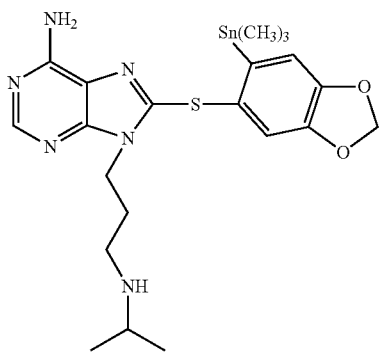

In some embodiments, PG is a protecting group that is capable of being removed under mildly basic conditions. In certain embodiments, PG is -Fmoc.

In some embodiments, the present invention provides a method comprising the steps of:

a) providing an aryl iodide compound:

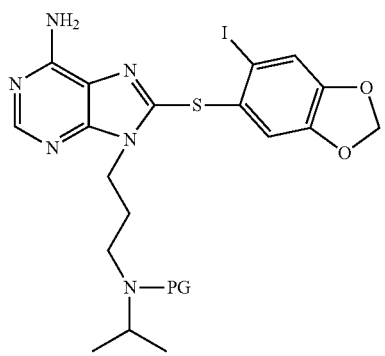

wherein PG is a suitable protecting group as defined above and described in classes and subclasses herein; and b) reacting the aryl iodide under suitable conditions to provide protected amine compound:

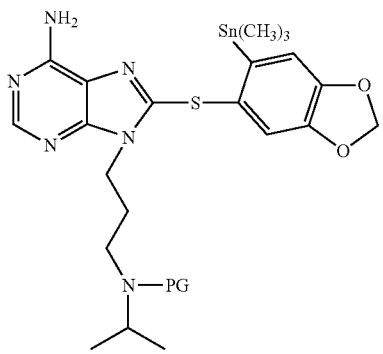

In some embodiments, the present invention provides a method comprising the steps of:

a) providing an aryl iodide of formula:

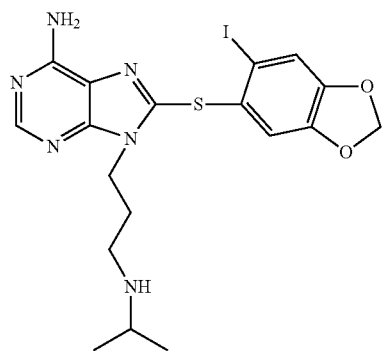 [SMILES: CC(C)NCCCn1c(Sc2cc3c(cc2I)OCO3)nc2c(N)ncnc21]

and b) reacting the aryl iodide under suitable reaction conditions to provide an aryl iodide of formula:

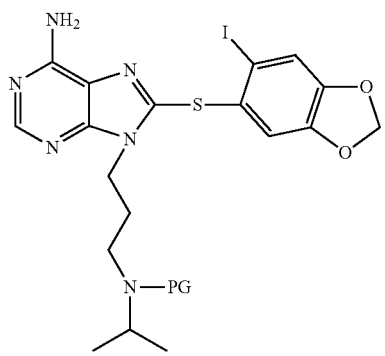

Pharmaceutical Compositions

In another aspect, the present invention provides pharmaceutical compositions comprising a Compound $I^L$ in combination with a pharmaceutically acceptable excipient (e.g., carrier). In some embodiments, such pharmaceutical compositions optionally include an aryl iodide of formula A.

The pharmaceutical compositions include optical isomers, diastereomers, or pharmaceutically acceptable salts of the inhibitors disclosed herein. Compound $I^L$ included in the pharmaceutical composition may be covalently attached to a carrier moiety, as described above. Alternatively, Compound $I^L$ included in the pharmaceutical composition is not covalently linked to a carrier moiety.

A "pharmaceutically acceptable carrier," as used herein refers to pharmaceutical excipients, for example, pharmaceutically, physiologically, acceptable organic or inorganic carrier substances suitable for enteral or parenteral application that do not deleteriously react with the active agent. Suitable pharmaceutically acceptable carriers include water, salt solutions (such as Ringer's solution), alcohols, oils, gelatins, and carbohydrates such as lactose, amylose or starch, fatty acid esters, hydroxymethycellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention.

The compounds of the invention can be administered alone or can be co-administered to the subject. Co-administration is meant to include simultaneous or sequential administration of the compounds individually or in combination (more than one compound). The preparations can also be combined, when desired, with other active substances (e.g. to reduce metabolic degradation).

Compounds of the present invention can be prepared and administered in a wide variety of oral, parenteral, and topical dosage forms. Thus, the compounds of the present invention can be administered by injection (e.g. intravenously, intramuscularly, intracutaneously, subcutaneously, intraduodenally, or intraperitoneally). Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substance that may also act as diluents, flavoring agents, binders, preservatives, tablet disintegrating agents, or an encapsulating material.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. The compounds of the invention can also be incorporated into liposomes or administered via transdermal pumps or patches. Pharmaceutical admixtures suitable for use in the present invention include those described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions of the present invention may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

In order that the invention described herein may be more fully understood, the following examples are set forth. It should be understood that these examples are for illustrative purposes only and are not to be construed as limiting this invention in any manner.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Example 1

Experimental Details for the Synthesis of Compound I-1 (Method 1)

One route to I-1 involves direct installation of the trimethyltin moiety onto PU-H71 (Method 1). The trimethyltin group is known to be unstable under acidic conditions and indeed, when 3 (see Scheme A, supra) was treated with dilute TFA (20% in $CH_2Cl_2$), protodestannylation occurred in addition to cleavage of the Boc protecting group.
Method 1

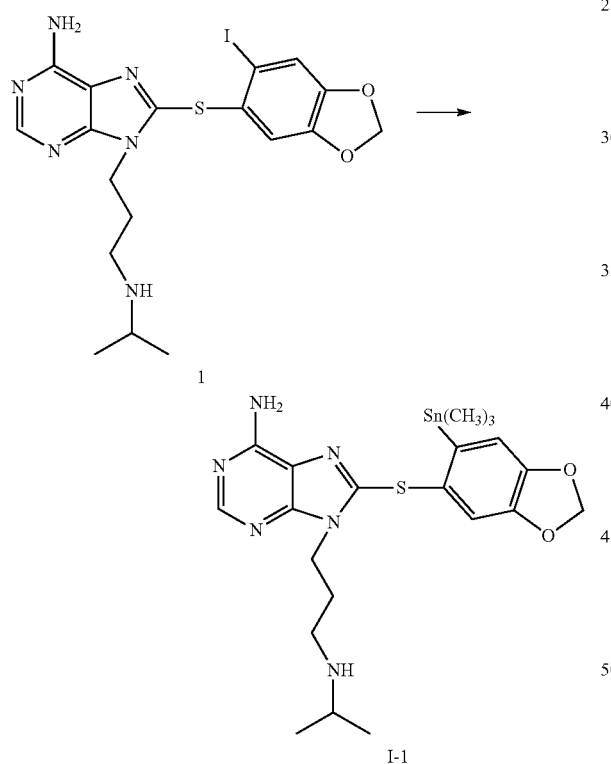

9-(3-(isopropylamino)propyl)-8-((6-(trimethylstannyl)benzo[d][1,3]dioxol-5-yl)thio)-9H-purin-6-amine (I-1). Compound 1 (30 mg, 0.0585 mmol), Pd(PPh$_3$)$_4$ (3.4 mg, 0.0029 mmol), hexamethylditin (48 µL, 0.232 mmol) in dry dioxane (3 mL) was heated at 90° C. in a 10 mL round-bottomed flask sealed with a rubber septum for 18 hours. The solvent was concentrated under vacuum and the crude product was purified via preparatory TLC (CHCl$_3$:EtOAc:hexane:NH$_3$/MeOH at 2:1:2:0.5) to afford I-1 (13.2 mg, 41%, average over four experiments). $^1$H NMR (500 MHz, CDCl$_3$) δ 8.26 (s, 1H), 7.02 (s, 1H), 6.98 (s, 1H), 5.98 (s, 2H), 5.63 (bs, 2H), 4.26 (t, J=6.8 Hz, 2H), 2.73 (m, 1H), 2.57 (t, J=6.8 Hz, 2H), 2.02 (m, 2H), 1.06 (d, J=10.6 Hz, 6H), 0.28 (s, 9H); LCMS found 551.2 [M+H]$^+$.

Example 2

Experimental Details for the Synthesis of Compound I-1 (Method 2)

Method 2 utilized a protecting group strategy as an alternative to Method 1. Fmoc was chosen since it can be removed under mildly basic conditions, and importantly the trimethyltin moiety is stable under these conditions.
Method 2

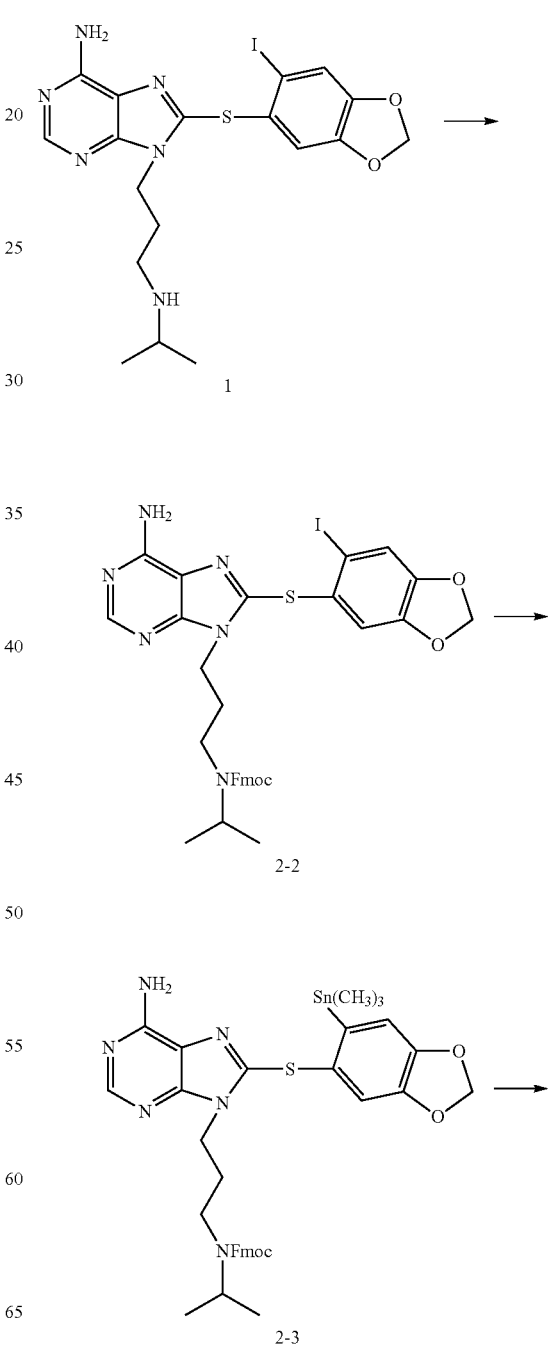

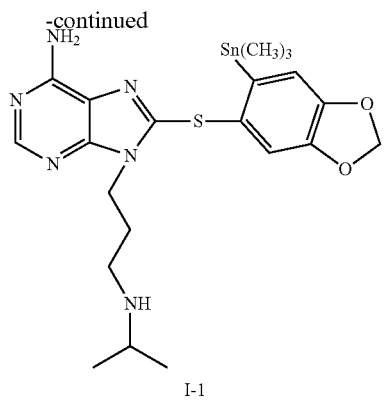

I-1

(9H-fluoren-9-yl)methyl (3-(6-amino-8-((6-iodobenzo[d][1,3]dioxol-5-yl)thio)-9H-purin-9-yl)propylisopropyl)carbamate (2-2). To compound 1 (100 mg, 0.195 mmol) in a mixture of THF/water (4 mL: 1 mL) and cooled in an ice bath, 9-Fluorenylmethyl N-succinimidyl carbonate (98.5 mg, 0.292 mmol) was added as a solid in one portion followed by the addition of solid sodium bicarbonate (24.5 mg, 0.292 mmol). The reaction mixture was stirred at room temperature for 3 hours. The reaction was determined to be complete by TLC and LC-MS, LCMS found 735.4 [M+H]$^+$. Then, the solvent was concentrated and the crude product was purified by preparatory TLC (DCM:MeOH 95:5) to afford 2-2 (126 mg, 88%). $^1$H NMR (500 MHz, DMSO-$d_6$) δ 8.14 (s, 1H), 7.83 (br. s, 2H), 7.57 (br. s, 2H), 7.46 (s, 1H), 7.25-7.40 (m, 6H), 6.77 (s, 1H), 6.02 (s, 2H), 4.45 (d, J=4.95 Hz, 2H), 4.19 (m, 1H), 4.08 (q, J=5.26 Hz, 2H), 3.83-3.89 (m, 2H), 3.03 (m, 1H) 2.76 (m, 1H), 1.78 (m, 1H), 0.76-0.85 (m, 6H).

(9H-fluoren-9-yl)methyl (3-(6-amino-8-((6-(trimethylstannyl)benzo[d][1,3]dioxol-5-yl)thio)-9H-purin-9-yl)propylXisopropyl)carbamate (2-3). Compound 2-2 (100 mg, 0.136 mmol), Pd(PPh$_3$)$_4$ (7.85 mg, 0.0068 mmol), hexamethylditin (178.2 mg, 0.544 mmol) in dry dioxane (6 mL) was heated at 90° C. in a 25 mL round-bottomed flask sealed with a rubber septum for 18 hours. The solvent was concentrated and the crude product purified via preparatory TLC (CHCl$_3$:EtOAc:hexane:NH$_3$/MeOH at 2:1:2:0.5) to afford 2-3 (58.8 mg, 56%). $^1$H NMR (500 MHz, CDCl$_3$) δ 8.24 (s, 1H), 7.74 (d, J=7.4 Hz, 2H), 7.65 (m, 1H), 7.54 (m, 2H), 7.46 (m, 1H), 7.35 (m, 2H), 7.28 (m, 3H), 6.95 (s, 1H), 5.93 (s, 2H), 5.65 (br. s., 2H), 4.55 (m, 2H), 4.21 (m, 2H), 3.83 (br s, 1H), 3.20 (m, 1H), 2.91 (m, 1H), 1.78 (m, 1H), 0.97 (d, J=4.9 Hz, 6H), 0.27 (s, 9H); LCMS found 773.4 [M+H]$^+$.

9-(3-(isopropylamino)propyl)-8-((6-(trimethylstannyl)benzo[d][1,3]dioxol-5-yl)thio)-9H-purin-6-amine (I-1). To compound 2-3 (12 mg, 0.0155 mmol) in dry CH$_2$Cl$_2$ (1.5 mL) was added diethylamine (265 mg, 375 μL, 3.62 mmol), and the reaction mixture was stirred at room temperature for 18 hours. Then, more diethylamine (318 mg, 450 μL, 4.35 mmol) was added to the reaction, and the reaction mixture stirred for 3 additional hours followed by LC-MS. After completion of the reaction the solvent was concentrated. The crude product was purified via preparatory TLC (CHCl$_3$:EtOAc:hexane:NH$_3$/MeOH at 2:1:2:0.5) to afford I-1 (5.7 mg, 70%). $^1$NMR (500 MHz, CDCl$_3$) δ 8.26 (s, 1H), 7.02 (s, 1H), 6.98 (s, 1H), 5.98 (s, 2H), 5.50 (br s, 2H), 4.26 (t, J=6.8 Hz, 2H), 2.73 (m, 1H), 2.57 (t, J=6.8 Hz, 2H), 2.02 (m, 2H), 1.05 (d, J=10.6 Hz, 6H), 0.28 (s, 9H); MS m/z 551.24 (M+H)+; 549.11 (M–H)$^-$. LCMS found 551.4 [M+H]$^+$.

Comparative Cost Analysis for the Synthesis of Compound I-1

In Method 1, when 1 was directly subjected to conditions that were previously used for Boc-protected 2, the desired product I-i in was obtained in 41% yield. Similarly, when Fmoc-protected PU-H71 2-2 was subjected to similar conditions 2-3 was obtained in 56% yield. Compared to the Method 1, Method 2 requires two additional steps, installation and removal of the Fmoc group, at yields of 88% and 70%, respectively. The overall yield for Method 2 is 34% (0.88×0.56×0.70×100%) which is comparable to Method 1.

[$^{124}$I]— NaI costs per mCi~$225, and a typical patient dose=5-11 mCi/study. To carry out the radiolabeling as depicted in Scheme A using a Boc precursor, the typical isolated yields are 40-50% and requires 2 or more hours of radiochemistry time (~$300), producing inconsistent results. In contrast, using compound I-1 as in Methods 1 and 2 above produces typical isolated yields in the range of 60-70% (i.e., 2 mCi of material saved), with radiochemistry time down to 30 min. or less. Moreover, these methods are more reliable and reproducible, which is highly desirable in clinical applications. Thus, the total savings per dose are currently estimated to be about $725 compared to the current methods. Method 1 offers the additional advantage of requiring fewer steps to produce compound I-1, which results in additional savings as compared to both Method 2 and the existing chemistry depicted in Scheme A.

Example 3

Radiolabeling of Compounds of Formula I

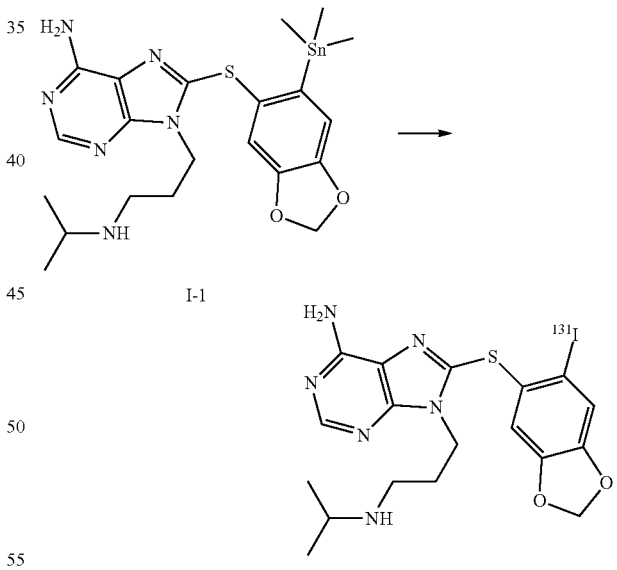

To a solution of 25 μl of compound I-1 (1.0 μg/μL in methanol) in Eppendorf was added [$^{131}$I]—NaI solution (0.4 mCi in 4 uL in 0.1N NaOH) and the solution was vortexed. To this solution, 2 μL of chloramine-T (2 mg/ml acetic acid) was added and the reaction mixture was vortexed and allowed to react for 1 min. The crude product was purified by passing through a C-18 column (Phenomenex, Luna 250×4.6 mm, 5μ, 110 Å), using 20% B (A=0.1% TFA; B=0.1% TFA in acetonitrile) as the eluant with a flow rate of 1 ml/min. The product has a retention time of about 12 minutes, under the conditions described above was collected and used for further studies. The yield for this reaction averages in the range of 60-70%.

Alternative Purification Procedure

Precondition Sep-Pak® Classic C18 cartridge (360 mg 55-105 μm) with 10 mL of ethanol and followed by 20 mL of water. Dilute the reaction mixture with 1 mL of water and load this diluted reaction mixture on to Sep-Pak® c18 cartridge. Wash the cartridge with 20 mL water (2×10 mL). The final product can be eluted in ethanol (<3 mL) from Sep-Pak® into a new vial. The ethanol volume can be reduced by inert gas flow to <0.3 mL. The product can be formulated in saline (5-10 mL) and sterile filtered to final product vial assembly.

Example 4

Preparation of Compound I-2

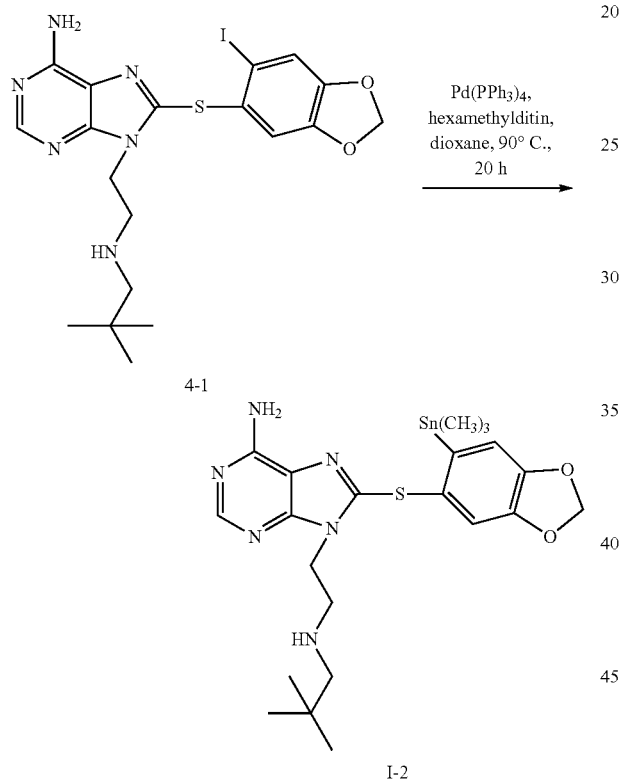

9-(2-(Neopentylamino)ethyl)-8-((6-(trimethylstannyl) benzo[d][1,3]dioxol-5-yl)thio)-9H-purin-6-amine (1-2). To compound 4-1 (25 mg, 0.047 mmol), Pd(PPh$_3$)$_4$ (2.7 mg, 0.0023 mmol), hexamethylditin (38.9 μL, 0.232 mmol) was added 3 mL of dry dioxane and the reaction mixture was heated at 90° C. in a 10 mL round-bottomed flask sealed with a rubber septum for 20 hours. The solvent was concentrated under vacuum and the crude product was purified via preparatory TLC twice; first time using CHCl$_3$:EtOAc: hexane:NH$_3$/MeOH (7N) at 2:1:2:0.5, and then by CH$_2$Cl$_2$: MeOH at 9:1 to afford I-2 (7.4 mg, 28%). $^1$H NMR (500 MHz, CD$_3$OD) □ 8.14 (s, 1H), 7.12 (s, 1H), 7.05 (s, 1H), 6.05 (s, 2H), 4.34 (t, J=6.6 Hz, 2H), 3.04 (t, J=6.6 Hz, 2H), 2.41 (s, 2H), 0.89 (s, 9H), 0.26 (s, 9H); MS (m/z): [M+H]$^+$ 565.2.

Radiolabeling of compound I-2 is carried out as described in Example 3, substituting compound I-2 for compound I-1.

Example 5

Preparation of Compound I-3

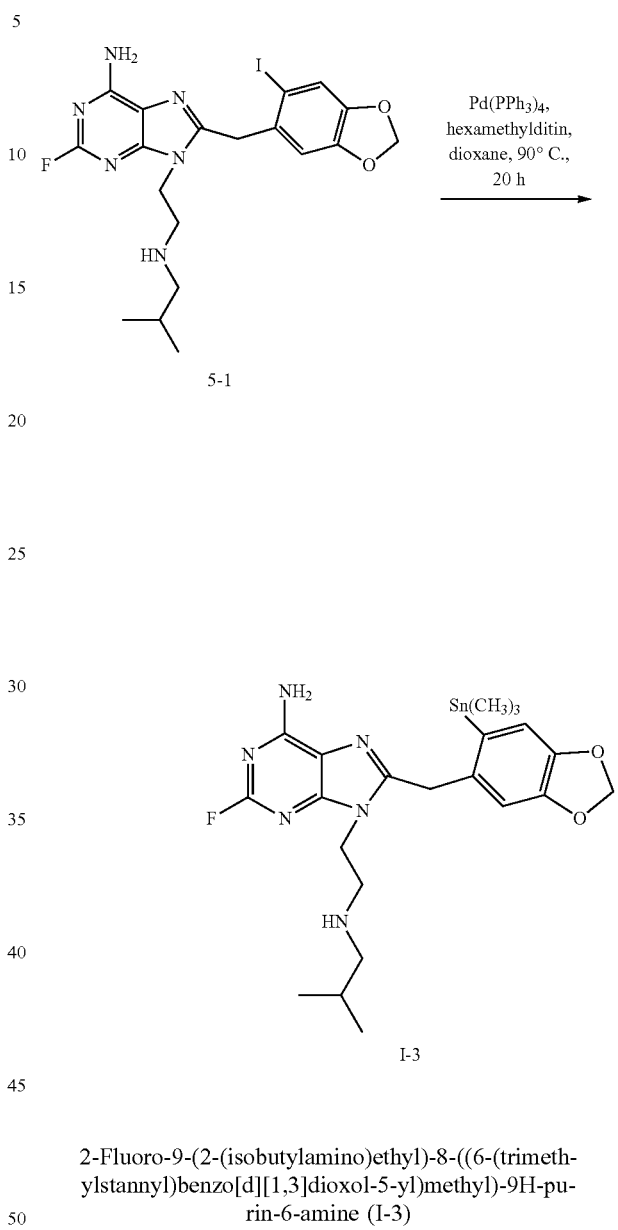

2-Fluoro-9-(2-(isobutylamino)ethyl)-8-((6-(trimethylstannyl)benzo[d][1,3]dioxol-5-yl)methyl)-9H-purin-6-amine (I-3)

To compound 5-1 (25 mg, 0.048 mmol), Pd(PPh$_3$)$_4$ (2.8 mg, 0.0024 mmol), and hexamethylditin (39.8 μL, 0.232 mmol) was added 3 mL of dry dioxane and the reaction mixture was heated at 90° C. in a 10 mL RBF sealed with a rubber septum for 20 hours. The solvent was concentrated under vacuum and the crude product was purified via preparatory TLC twice, first by using CHCl$_3$:EtOAc:hexane: NH$_3$/MeOH (7N) at 2:1:2:0.5, and then CH$_2$Cl$_2$:MeOH at 9:1 to afford I-3 (4.6 mg, 17%). $^1$H NMR (500 MHz, CD$_3$OD) □ 6.95 (s, 1H), 6.69 (s, 1H), 5.92 (s, 2H), 4.24 (s, 2H), 4.21 (t, J=6.6 Hz, 2H), 2.90 (t, J=6.6 Hz, 2H), 2.40 (d, J=6.4 Hz, 2H), 1.70 (m, 1H), 0.89 (d, J=6.5 Hz, 6H), 0.26 (s, 9H); MS (m/z): [M+H]$^+$ 551.2.

Radiolabeling of compound I-3 is carried out as described in Example 3, substituting compound I-3 for compound I-1.

Example 6

Preparation of Compound I-4

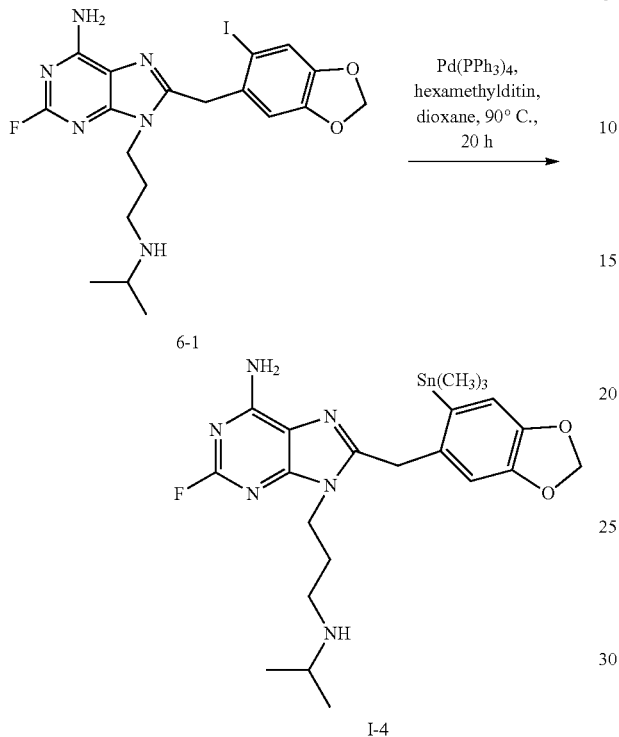

2-Fluoro-9-(3-(isopropylamino)propyl)-8-((6-(trimethylstannyl)benzo[d][1,3]dioxol-5-yl)methyl)-9H-purin-6-amine (I-4). To compound 6-1 (25 mg, 0.0487 mmol), Pd(PPh$_3$)$_4$ (2.81 mg, 0.0024 mmol), and hexamethylditin (40 μL, 0.194 mmol) was added 3 mL of dry dioxane and the reaction mixture was heated at 90° C. in a 10 mL round-bottomed flask sealed with a rubber septum for 20 hours. The solvent was concentrated under vacuum and the crude product was purified via preparatory TLC twice; first time using CHCl$_3$:EtOAc:hexane:NH$_3$/MeOH (7N) at 2:1:2:0.5, and then by CH$_2$Cl$_2$:MeOH at 9:1 to afford I-4 (4.5 mg, 17%). $^1$H NMR (500 MHz, CD$_3$OD) □ 6.96 (s, 1H), 6.70 (s, 1H), 5.92 (s, 2H), 4.22 (s, 2H), 4.19 (t, J=7.1 Hz, 2H), 2.90 (m, 1H), 2.67 (t, J=7.1 Hz, 2H), 1.97 (m, 2H), 1.13 (d, J=6.2 Hz, 6H), 0.21 (s, 9H); MS (m/z): [M+H]$^+$ 551.2.

Radiolabeling of compound I-4 is carried out as described in Example 3, substituting compound I-4 for compound I-1.

What is claimed is:

1. A method of administering a radiolabeled compound to a patient comprising administering to a patient in need thereof an amount of a compound of Formula I$^L$:

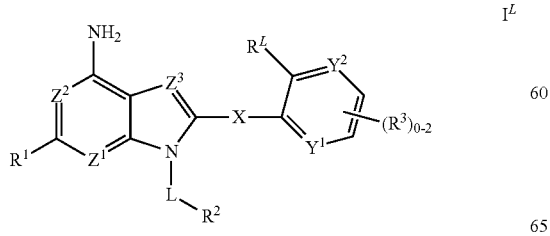

or a pharmaceutically acceptable salt thereof, wherein:
X is CH$_2$—, —O—, or —S—;
Y$^1$ and Y$^2$ are independently —CR$^{3a}$— or —N—;
Z$^1$, Z$^2$, and Z$^3$ are independently —CH— or —N—;
R$^1$ is hydrogen or halogen;
L is a straight or branched, C$_{2-14}$ aliphatic group wherein one or more carbons are optionally and independently replaced by -Cy-, —NR—, —N(R)C(O)—, —C(O)N(R)—, —C(O)N(O)—, —N(R)SO$_2$—, —SO$_2$N(R)—, —O—, —C(O)—, —OC(O)—, —C(O)O—, —S—, —SO—, or —SO$_2$—,
each -Cy- is independently an optionally substituted 3-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
R$^2$ is hydrogen or an optionally substituted group selected from the group consisting of C$_{1-6}$ aliphatic, phenyl, 3- to 7-membered saturated or partially unsaturated monocyclic carbocyclyl, 3- to 7-membered saturated or partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, 7- to 10-membered saturated or partially unsaturated bicyclic carbocyclyl, 7- to 10-membered saturated or partially unsaturated bicyclic heterocyclyl having 1-4 heteroatoms selected from oxygen, nitrogen, or sulfur, 7- to 10-membered bicyclic heteroaryl having 1-4 heteroatoms selected from oxygen, nitrogen, or sulfur, or 8- to 10-membered bicyclic aryl;
each R$^3$ is independently halogen, —NO$_2$, —CN, —OR, —SR, —N(R)$_2$, —C(O)R, —CO$_2$R, —C(O)C(O)R, —C(O)CH$_2$C(O)R, —S(O)R, —S(O)$_2$R, —C(O)N(R)$_2$, —SO$_2$N(R)$_2$, —OC(O)R, —N(R)C(O)R, —N(R)N(R)$_2$, or optionally substituted C$_{1-6}$ aliphatic or pyrrolyl; or
two R$^3$ groups are taken together with their intervening atoms to form Ring A, wherein Ring A is a 3- to 7-membered partially unsaturated carbocyclyl, phenyl, a 5- to 6-membered partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, or 6-membered aryl;
R$^{3a}$ is R$^3$ or hydrogen;
each R is independently hydrogen or an optionally substituted group selected from C$_{1-6}$ aliphatic, phenyl, 3- to 7-membered saturated or partially unsaturated carbocyclyl, 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur, or:
two R groups on the same nitrogen are taken together with their intervening atoms to form an optionally substituted ring selected from 3- to 7-membered saturated or partially unsaturated monocyclic heterocyclyl having 1-2 heteroatoms selected from oxygen, nitrogen, or sulfur, or 5- to 6-membered heteroaryl having 1-4 heteroatoms selected from oxygen, nitrogen, or sulfur;
$R^L$ is a radiolabel;
with the proviso that compound $I^L$ is not

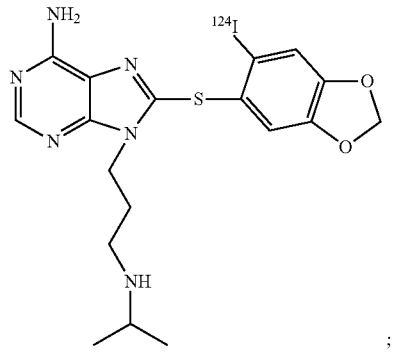 [SMILES: CC(C)NCCCn1c(Sc2cc3c(cc2[124I])OCO3)nc2c(N)ncnc21]
;

wherein the compound is administered intravenously, intramuscularly, intracutaneously, subcutaneously, intraduodenally, or intraperitoneally.

2. The method of claim 1, with the proviso that compound $I^L$ is not

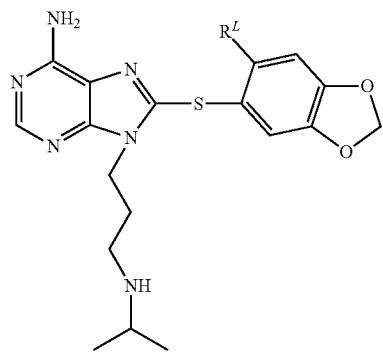
, wherein $R^L$ is a radiolabel.

3. The method of claim 2, wherein $Z^1$, $Z^2$, and $Z^3$ are —N—.

4. The method of claim 3, wherein $Y^1$ is —$CR^{3a}$—.

5. The method of claim 4, wherein $Y^2$ is —$CR^{3a}$—.

6. The method of claim 5, wherein each of $R^{3a}$ is hydrogen.

7. The method of claim 6, wherein X is —$CH_2$— or —S—.

8. The method of claim 7, wherein X is —$CH_2$—.

9. The method of claim 7, wherein X is —S—.

10. The method of claim 7, wherein $R^1$ is hydrogen.

11. The method of claim 7, wherein $R^1$ is halogen.

12. The method of claim 11, wherein $R^1$ is fluoro.

13. The method of claim 6, wherein -L-$R^2$ comprises a methylene that is replaced with —NH— to form a secondary amine.

14. The method of claim 7, wherein L is a $C_{2-14}$ aliphatic group, wherein a methylene of the aliphatic group is replaced with —NH— to form a secondary amine.

15. The method of claim 14, wherein L is a $C_{2-8}$ aliphatic group, wherein a methylene of the aliphatic group is replaced with —NH— to form a secondary amine.

16. The method of claim 6, wherein -L-$R^2$ is selected from the following:

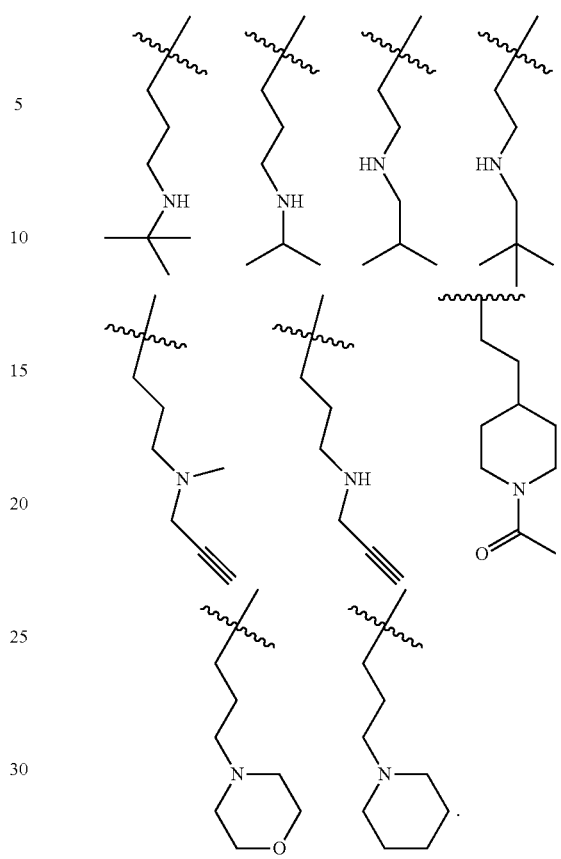

17. The method of claim 16, wherein -L-$R^2$ is selected from the following:

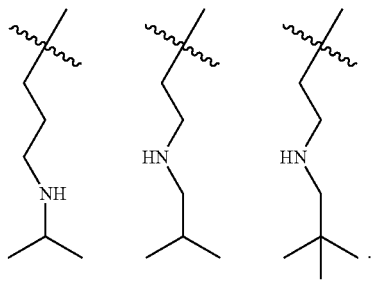

18. The method of claim 6, wherein two $R^3$ groups are taken together with their intervening atoms to form Ring A, wherein Ring A is a 5- to 6-membered partially unsaturated monocyclic heterocyclyl having 1-2 heteroatoms selected from oxygen, nitrogen, or sulfur, 5- to 6-membered heteroaryl having 1-4 heteroatoms selected from oxygen, nitrogen, or sulfur, or 6-membered aryl.

19. The method of claim 18, wherein Ring A is a 5-membered partially unsaturated monocyclic heterocyclyl having 2 heteroatoms selected from oxygen.

20. The method of claim 18, wherein Ring A is phenyl.

21. The method of claim 6, wherein two $R^3$ groups are taken together with their intervening atoms to form Ring A, wherein Ring A is 3- to 7-membered partially unsaturated carbocyclyl.

22. The method of claim 21, wherein Ring A is 5- to 6-membered partially unsaturated carbocyclyl.

23. The method of claim 15, wherein $R^L$ is selected from the group consisting of $^{131}$I, $^{125}$I, $^{124}$I, $^{123}$I, $^{11}$C, $^{15}$O, $^{13}$N, $^{19}$F and $^{18}$F.

24. The method of claim 23, wherein $R^L$ is $^{124}$I.

* * * * *